(12) United States Patent
Baker, Jr. et al.

(10) Patent No.: US 8,668,911 B2
(45) Date of Patent: Mar. 11, 2014

(54) STREPTOCOCCUS VACCINE COMPOSITIONS AND METHODS OF USING THE SAME

(75) Inventors: James R. Baker, Jr., Ann Arbor, MI (US); Paul E. Makidon, Webberville, MI (US); Whitney A. Dunlap, Jacksonville, FL (US); Jessica A. Knowlton, Cordova, TN (US); Benjamin Swanson, Ann Arbor, MI (US)

(73) Assignee: The Regents Of The University Of Michigan, Ann Arbor, MI (US)

( * ) Notice: Subject to any disclaimer, the term of this patent is extended or adjusted under 35 U.S.C. 154(b) by 0 days.

(21) Appl. No.: 13/320,205

(22) PCT Filed: May 14, 2010

(86) PCT No.: PCT/US2010/034999
§ 371 (c)(1),
(2), (4) Date: Feb. 13, 2012

(87) PCT Pub. No.: WO2010/132833
PCT Pub. Date: Nov. 18, 2010

(65) Prior Publication Data
US 2012/0128719 A1 May 24, 2012

Related U.S. Application Data

(60) Provisional application No. 61/178,344, filed on May 14, 2009.

(51) Int. Cl.
*A61K 39/09* (2006.01)
(52) U.S. Cl.
USPC .................................. 424/236.1; 424/244.1

(58) Field of Classification Search
None
See application file for complete search history.

(56) References Cited

U.S. PATENT DOCUMENTS

| | | | |
|---|---|---|---|
| 4,596,792 | A | 6/1986 | Vyas |
| 4,599,230 | A | 7/1986 | Milich et al. |
| 4,599,231 | A | 7/1986 | Milich et al. |

(Continued)

FOREIGN PATENT DOCUMENTS

| | | |
|---|---|---|
| EP | 0372501 | 6/1990 |
| EP | 0378881 | 7/1990 |

(Continued)

OTHER PUBLICATIONS

Baraldo et al., N19 polyepitope as a carrier for enhanced immunogenicity and protective efficacy of meningococcal conjugate vaccines, Infect Immun. Aug. 2004;72(8):4884-7.

(Continued)

*Primary Examiner* — Albert Navarro
*Assistant Examiner* — Ginny Portner
(74) *Attorney, Agent, or Firm* — Tyler J. Sisk; Casimir Jones S.C.

(57) ABSTRACT

The present invention provides methods and compositions for the stimulation of immune responses. In particular, the present invention provides immunogenic nanoemulsion compositions and methods of using the same for the induction of immune responses (e.g., innate and/or adaptive immune responses (e.g., for generation of host immunity against a bacterial species of the genus *Streptococcus* (e.g., *Streptococcus pneumoniae*))). Compositions and methods of the present invention find use in, among other things, clinical (e.g. therapeutic and preventative medicine (e.g., vaccination)) and research applications.

5 Claims, 12 Drawing Sheets

(56) References Cited

U.S. PATENT DOCUMENTS

| | | | |
|---|---|---|---|
| 4,601,903 | A | 7/1986 | Frasch |
| 4,709,017 | A | 11/1987 | Collier et al. |
| 4,895,452 | A | 1/1990 | Yiournas et al. |
| 4,950,740 | A | 8/1990 | Greenfield et al. |
| 5,103,497 | A | 4/1992 | Hicks |
| 5,547,677 | A | 8/1996 | Wright |
| 5,549,901 | A | 8/1996 | Wright |
| 5,618,840 | A | 4/1997 | Wright |
| 5,700,679 | A | 12/1997 | Wright |
| 5,716,637 | A * | 2/1998 | Anselem et al. ............... 424/450 |
| 5,843,711 | A | 12/1998 | Collier et al. |
| 5,917,017 | A | 6/1999 | Collier et al. |
| 6,015,832 | A | 1/2000 | Baker, Jr. et al. |
| 6,042,838 | A * | 3/2000 | Briles et al. ................ 424/244.1 |
| 6,287,555 | B1 * | 9/2001 | Gill et al. ..................... 424/93.1 |
| 6,455,673 | B1 | 9/2002 | Collier |
| 6,506,803 | B1 | 1/2003 | Baker, Jr. et al. |
| 6,559,189 | B2 | 5/2003 | Baker, Jr. et al. |
| 6,635,676 | B2 | 10/2003 | Baker, Jr. et al. |
| 7,314,624 | B2 * | 1/2008 | Baker et al. ................. 424/192.1 |
| 8,236,335 | B2 * | 8/2012 | Baker et al. ................... 424/405 |
| 2002/0045667 | A1 | 4/2002 | Baker, Jr. et al. |
| 2002/0155084 | A1 * | 10/2002 | Roessler et al. ........... 424/70.21 |
| 2004/0043041 | A1 | 3/2004 | Baker, Jr. et al. |
| 2005/0208038 | A1 * | 9/2005 | Fischetti et al. .......... 424/94.63 |
| 2005/0208083 | A1 | 9/2005 | Annis |
| 2005/0281843 | A1 | 12/2005 | Singh et al. |
| 2006/0251684 | A1 * | 11/2006 | Annis et al. .................... 424/400 |
| 2006/0257426 | A1 * | 11/2006 | Baker et al. ................. 424/204.1 |
| 2007/0036831 | A1 | 2/2007 | Baker |
| 2008/0181949 | A1 * | 7/2008 | Baker et al. .................... 424/484 |
| 2008/0254066 | A1 * | 10/2008 | Baker et al. ................. 424/206.1 |
| 2008/0292663 | A1 * | 11/2008 | Gerber ........................ 424/280.1 |
| 2008/0317799 | A1 | 12/2008 | Baker et al. |
| 2009/0291095 | A1 * | 11/2009 | Baker et al. ................. 424/184.1 |
| 2010/0021504 | A1 * | 1/2010 | Gibson et al. .............. 424/244.1 |
| 2012/0141526 | A1 * | 6/2012 | Baker et al. ................. 424/208.1 |

FOREIGN PATENT DOCUMENTS

| | | |
|---|---|---|
| EP | 0427347 | 5/1991 |
| EP | 0471177 | 2/1992 |
| WO | 91/01146 | 2/1991 |
| WO | 91/18926 | 12/1991 |
| WO | 93/17712 | 9/1993 |
| WO | 94/00153 | 1/1994 |
| WO | 94/03208 | 2/1994 |
| WO | 95/17210 | 6/1995 |
| WO | 96/33739 | 10/1996 |
| WO | 98/56414 | 12/1998 |
| WO | 98/58668 | 12/1998 |
| WO | 99/11241 | 3/1999 |
| WO | 99/12565 | 3/1999 |
| WO | 00/37105 | 6/2000 |
| WO | 00/56360 | 6/2000 |
| WO | 00/39299 | 7/2000 |
| WO | 00/61761 | 10/2000 |
| WO | 01/72337 | 10/2001 |
| WO | 01/98334 | 12/2001 |
| WO | 02/091998 | 11/2002 |
| WO | 03/054007 | 7/2003 |
| WO | 2004/081515 | 9/2004 |
| WO | WO 2007/120860 A2 * | 10/2007 |

OTHER PUBLICATIONS

Classen et al., Detection of antibody to murine cytomegalovirus by enzyme-linked immunosorbent and indirect immunofluorescence assays, J Clin Microbiol. Apr. 1987;25(4):600-4.

Donovan et al., Prevention of murine influenza A virus pneumonitis by surfactant nano-emulsions. Antiviral Chemistry and Chemotherapy, 2000, vol. 11, pp. 41-49.

Falugi et al., Rationally designed strings of promiscuous CD4(+) T cell epitopes provide help to *Haemophilus influenzae* type B oligosaccharide: a model for new conjugate vaccines, Eur J Immunol. Dec. 2001;31(12):3816-24.

Frey et al., A statistically defined endpoint titer determination method for immunoassays, J Immunol Methods. Dec. 1, 1998;221(1-2):35-41.

Hamouda and Baker, Antimicrobial mechanism of action of surfactant lipid preparations in enteric Gram-negative Bacilli, J. Appl. Microbiol., 89:397-403 (2000).

Hamouda et al., A Novel Surfactant nanoemulsion with Broad-Spectrum Sporicidal Activity against *Bacillus* Species, J. Infect Dis., 180:1939-1949 (1999).

Kuo et al., Characterization of a recombinant pneumolysin and its use as a protein carrier for pneumococcal type 18C conjugate vaccines, Infect Immun. Jul. 1995;63(7):2706-13.

Lupas et al., Predicting coiled coils from protein sequences, Science. May 24, 1991;252(5010):1162-4.

Malley et al., Intranasal immunization with killed unencapsulated whole cells prevents colonization and invasive disease by capsulated pneumococci, Infect Immun. Aug. 2001;69(8):4870-3.

Malley et al., Multiserotype protection of mice against pneumococcal colonization of the nasopharynx and middle ear by killed nonencapsulated cells given intranasally with a nontoxic adjuvant, Infect Immun. Jul. 2004;72(7):4290-2.

Malley et al., CD4+ T cells mediate antibody-independent acquired immunity to pneumococcal colonization, Proc Natl Acad Sci U S A. Mar. 29, 2005;102(13):4848-53. Epub Mar. 21, 2005.

Mestecky, The common mucosal immune system and current strategies for induction of immune responses in external secretions, J Clin Immunol. Jul. 1987;7(4):265-76.

Morrison et al., Chimeric human antibody molecules: mouse antigen-binding domains with human constant region domains, Proc Natl Acad Sci U S A. Nov. 1984;81(21):6851-5.

Neuberger et al., Recombinant antibodies possessing novel effector functions, Nature. Dec. 13-19, 1984;312 (5995):604-8.

Roghmann et al., Immune response of elderly adults to pneumococcus: variation by age, sex, and functional impairment, J Gerontol. May 1987;42(3):265-70.

Takeda et al., Construction of chimaeric processed immunoglobulin genes containing mouse variable and human constant region sequences, Nature. Apr. 4-10, 1985;314(6010):452-4.

Uchida et al., Diphtheria toxin and related proteins. I. Isolation and properties of mutant proteins serologically related to diphtheria toxin, J Biol Chem. Jun. 10, 1973;248(11):3838-44.

Verghese and Berk, Bacterial pneumonia in the elderly, Medicine (Baltimore). Sep. 1983;62(5):271-85.

\* cited by examiner

FIGURE 1

| Reconstituted with 300μl water: | # doses to mix | Ag/ Mouse (μl) | Ag group total (mL) | H₂O/ Mouse (μl) | H₂O group total (mL) | 60%NE/ Mouse (μl) | 60%NE group total (mL) | 10X PBS /Mouse | 10xPBS group total (mL) | 1XPBS (μl) | 1XPBS group tot (mL) | ALUM | Alum group tot (mL) | CT | CT group total (μL) | Cells per innoculation | Volume of innoculation | # of mice |
|---|---|---|---|---|---|---|---|---|---|---|---|---|---|---|---|---|---|---|
| 1% NE | 10 | 7.50 | 75.00 | 3.85 | 38.50 | 0.20 | 2.00 | 0.45 | 4.50 | | | | | | | 1x10⁸ | 12.00 | 6 |
| 5% NE | 18 | 7.50 | 135.00 | 3.05 | 54.90 | 1.00 | 18.00 | 0.45 | 81.00 | | | | | | | 1x10⁸ | 12.00 | 14 |
| 10% NE | 10 | 7.50 | 75.00 | 2.05 | 20.50 | 2.00 | 20.00 | 0.45 | 4.50 | | | | | | | 1x10⁸ | 12.00 | 6 |
| 20% NE | 10 | 7.50 | 75.00 | 0.05 | 0.50 | 4.00 | 40.00 | 0.45 | 4.50 | | | | | | | 1x10⁸ | 12.00 | 6 |
| total recon vol (incl control) | 570 | | | | | | | | | | | | | | | | | |
| Reconstituted with 400μl water: | | | | | | | | | | | | | | | | | | |
| 1% NE | 10 | 0.10 | 1.00 | 10.53 | 105.30 | 0.17 | 1.70 | 1.20 | 12.00 | | | | | | | 1x10⁶ | 12.00 | 6 |
| 5% NE | 10 | 0.10 | 1.00 | 9.67 | 98.70 | 0.83 | 8.30 | 1.20 | 12.00 | | | | | | | 1x10⁶ | 12.00 | 6 |
| 10% NE | 10 | 0.10 | 1.00 | 9.03 | 90.30 | 1.67 | 16.70 | 1.20 | 12.00 | | | | | | | 1x10⁶ | 12.00 | 5 |
| 20% NE | 10 | 0.10 | 1.00 | 7.37 | 73.70 | 3.33 | 33.30 | 1.20 | 12.00 | | | | | | | 1x10⁶ | 12.00 | 6 |
| total reconstituted | 5 | | | | | | | | | | | | | | | | | |

| volume (including control) | | | | | | | | | | | | | |
|---|---|---|---|---|---|---|---|---|---|---|---|---|---|
| Control | 12 | | | | | | | | | | | | |
| 0.1 Ag+ 1x PBS | 12 | 0.10 | 1.20 | | | | 11.90 | | | | $1\times10^6$ | | 8 |
| 7.5 Ag+ 1xPBS | 18 | 7.50 | 135.00 | | | | 4.50 | 81.00 | | | $1\times10^8$ | 12.00 | 14 |
| 7.5 Ag + Alum IM | 4 | 7.50 | 30.00 | | | | | 170.00 | 25μg | 7μL | $1\times10^8$ | 50μl | 2 |
| 20% NE alone | 6 | | | 8.00 | 48.00 | 4.00 | 24.00 | | | | 0.00 | 12.00 | 4 |
| 7.5 Ag+ CT | 6 | 7.50 | 45.00 | | | | | | 1μg | 19.8μL | $1\times10^8$ | 12.00 | 4 |

FIGURE 1 CONTINUED

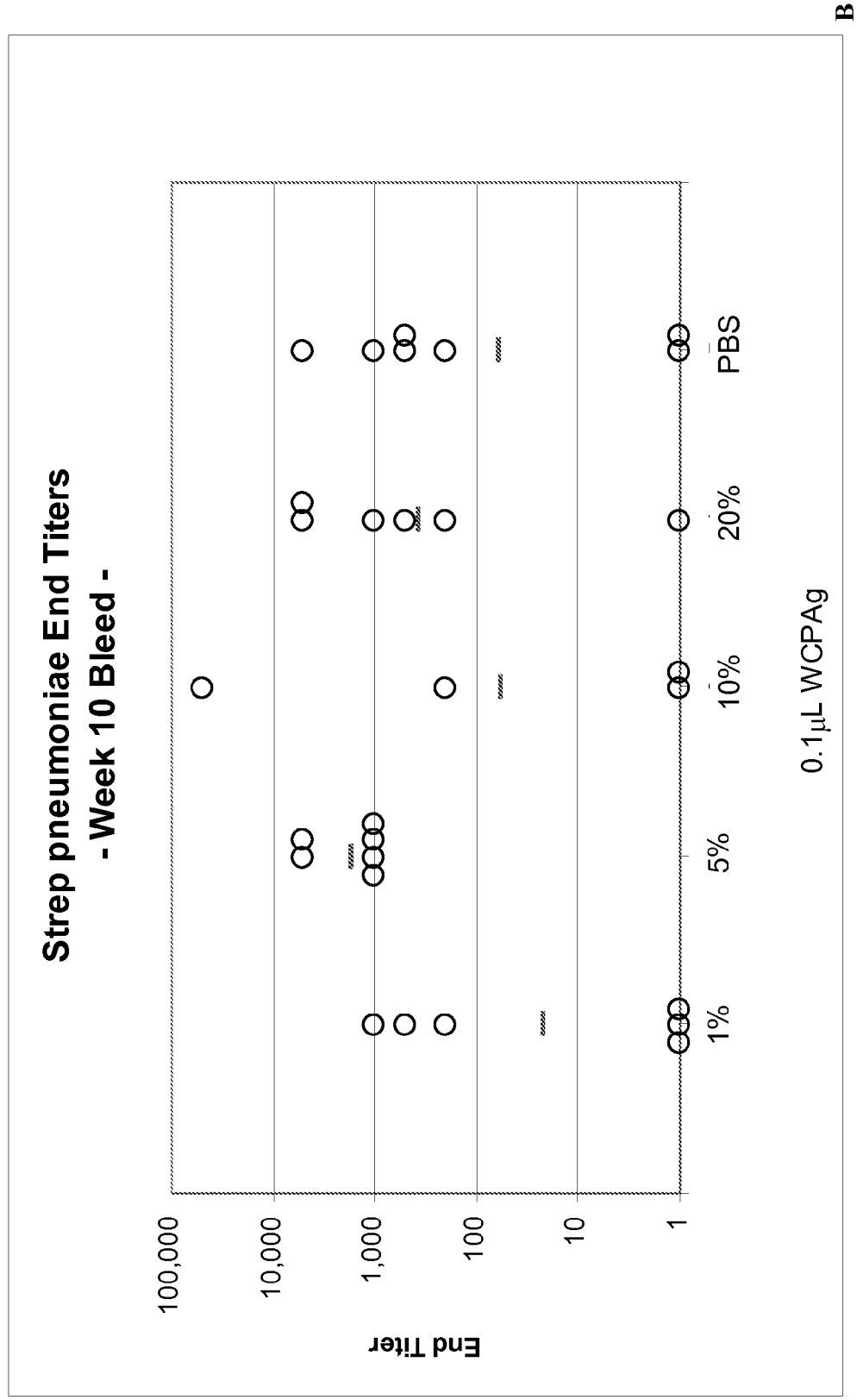

FIGURE 6

| Table 2. | Colony Count After Incubation with $W_{80}5EC$ | | | | |
|---|---|---|---|---|---|
| Time Point | PBS | 1% | 5% | 10% | 20% |
| 30 Minutes | TNTC | 0 | 0 | 0 | 0 |
| 1 Hour | TNTC | 0 | 0 | 0 | 0 |
| 3 Hours | TNTC | 0 | 0 | 0 | 0 |

FIGURE 7

| Table 2. Activity 2 study design | | | | | | |
|---|---|---|---|---|---|---|
| Group | Adjuvant | Cells/inoculum | Inoculum vol (µL) | Route | # mice | Strain |
| treatment | 5% NE | $10^7$ | 12 | IN | 8 | CD1 |
| treatment | 15% NE | $10^7$ | 12 | IN | 8 | CD1 |
| treatment | 5% NE | $10^9$ | 12 | IN | 8 | CD1 |
| treatment | 15% NE | $10^9$ | 12 | IN | 8 | CD1 |
| control | 15% NE | $10^9$ EI | 12 | IN | 8 | CD1 |
| control | Alum | $10^9$ EI | 50 | IM | 8 | CD1 |
| control | PBS | $10^9$ EI | 12 | IN | 8 | CD1 |
| control | 15% | 0 | 12 | IN | 8 | CD1 |
| control | 0 | 0 | 0 | | 8 | CD1 |
| | | | | | | |

US 8,668,911 B2

STREPTOCOCCUS VACCINE COMPOSITIONS AND METHODS OF USING THE SAME

The present application is a national phase application under 35 U.S.C. §371 of PCT International Application No. PCT/US2010/034999, filed on 14 May 2010, which claims priority to U.S. Provisional Patent Application Ser. No. 61/178,344 filed 14 May 2009, each of which is hereby incorporated by reference in its entirety.

FIELD OF THE INVENTION

The present invention provides methods and compositions for the stimulation of immune responses. In particular, the present invention provides immunogenic nanoemulsion compositions and methods of using the same for the induction of immune responses (e.g., innate and/or adaptive immune responses (e.g., for generation of host immunity against a bacterial species of the genus Streptococcus (e.g., Streptococcus pneumoniae))). Compositions and methods of the present invention find use in, among other things, clinical (e.g. therapeutic and preventative medicine (e.g., vaccination)) and research applications.

BACKGROUND

Immunization is a principal feature for improving the health of people. Despite the availability of a variety of successful vaccines against many common illnesses, infectious diseases remain a leading cause of health problems and death. Significant problems inherent in existing vaccines include the need for repeated immunizations, and the ineffectiveness of the current vaccine delivery systems for a broad spectrum of diseases.

In order to develop vaccines against pathogens that have been recalcitrant to vaccine development, and/or to overcome the failings of commercially available vaccines due to expense, complexity, and underutilization, new methods of antigen presentation must be developed which will allow for fewer immunizations, more efficient usage, and/or fewer side effects to the vaccine.

SUMMARY OF THE INVENTION

The present invention provides methods and compositions for the stimulation of immune responses. In particular, the present invention provides immunogenic nanoemulsion compositions and methods of using the same for the induction of immune responses (e.g., innate and/or adaptive immune responses (e.g., for generation of host immunity against a bacterial species of the genus Streptococcus (e.g., Streptococcus pneumoniae))). Compositions and methods of the present invention find use in, among other things, clinical (e.g. therapeutic and preventative medicine (e.g., vaccination)) and research applications.

In some embodiments, the present invention provides an immunogenic composition comprising a nanoemulsion and one or more Streptococcus antigens (e.g., Streptococcus pneumoniae antigens). In some embodiments, the nanoemulsion comprises an aqueous phase, an oil phase, and a solvent. The present invention is not limited by the type of nanoemulsion composition. Indeed, a variety of nanoemulsion compositions find use in the present invention including, but not limited to, those described herein. The present invention is not limited by the one or more Streptococcus antigens utilized in the immunogenic compositions and methods of the invention. Indeed, a variety of Streptococcus antigens may be utilized including, but not limited to, Streptococcal bacteria inactivated and/or killed by nanoemulsion (NE), killed and/or inactivated Streptococcus bacteria (e.g., via mixing with alcohol (e.g., ethanol)), whole cell lysates of a Streptococcus bacteria, one or more isolated, purified and/or recombinant Streptococcus proteins and/or protein fragments, or other type of Streptococcus antigen described herein. In a preferred embodiment, the Streptococcus antigen is killed Streptococcus pneumoniae (e.g., (See, e.g., Malley et al., (2001) Infect. Immun. 69, 4870-4873; Malley et al., (2004) Infect. Immun. 72, 4290-4292)). In some embodiments, a Streptococcus antigen composition comprises one or more adjuvants (e.g., cholera toxin (CT)). The present invention is not limited by the strain and/or serotype of Streptococcus pneumoniae utilized. A number of strains and/or serotypes of Streptococcus pneumoniae are described herein, each of which finds use in an immunogenic composition comprising a nanoemulsion and one or more Streptococcus antigens. In some embodiments, the immunogenic composition comprises nanoemulsion inactivated bacteria of the genus Streptococcus (e.g., Streptococcus pneumoniae). In some embodiments, the nanoemulsion is $W_{80}5EC$, although the present invention is not so limited. For example, in some embodiments, the nanoemulsion is selected from one of the nanoemulsion formulations described herein. In some embodiments, the composition comprises between 1-50% nanoemulsion solution, although greater and lesser amounts also find use in the invention. For example, in some embodiments, the immunogenic composition comprises about 1.0%-10%, about 10%-20%, about 20%-30%, about 30%-40%, about 40%-50%, about 50%-60% or more nanoemulsion solution. In some embodiments, the immunogenic composition comprises about 10% nanoemulsion solution. In some embodiments, the immunogenic composition comprises about 15% nanoemulsion solution. In some embodiments, the immunogenic composition comprises about 20% nanoemulsion solution. In some embodiments, the immunogenic composition comprises about 12% nanoemulsion solution. In some embodiments, the immunogenic composition comprises about 8% nanoemulsion solution. In some embodiments, the immunogenic composition comprises about 5% nanoemulsion solution. In some embodiments, the immunogenic composition comprises about 2% nanoemulsion solution. In some embodiments, the immunogenic composition comprises about 1% nanoemulsion solution. In some embodiments, an immunogenic composition (e.g., that is administered to a subject in order to generate a Streptococcus specific immune response in the subject) comprises $10^6$ colony forming units (CFU) of killed Streptococcus (e.g., $10^6$ CFU of Streptococcus pneumoniae bacteria prior to killing/inactivation of the bacteria), although greater (e.g., about $4 \times 10^6$ CFU, $8 \times 10^6$ CFU, $1 \times 10^7$ CFU, $2 \times 10^7$ CFU, $4 \times 10^7$ CFU, $8 \times 10^7$ CFU, $1 \times 10^8$ CFU, $1 \times 10^9$ CFU, or more CFU of killed Streptococcus) and lesser (e.g., about $1 \times 10^6$ CFU, $5 \times 10^5$ CFU, $1 \times 10^5$ CFU, $5 \times 10^4$ CFU, $1 \times 10^4$ CFU, $5 \times 10^3$ CFU, $1 \times 10^3$ CFU or fewer CFU of killed Streptococcus) amounts may also be utilized. In some embodiments, the composition is stable (e.g., at room temperature (e.g., for 12 hours, one day, two days, three days, four days, a week, two weeks, three weeks, a month, two months, three months, four months, five months, six months, 9 months, a year or more). In some embodiments, the immunogenic composition comprises a pharmaceutically acceptable carrier. The present invention is not limited to any particular pharmaceutically acceptable carrier. Indeed, any suitable carrier may be utilized including but not limited to those described herein. In some embodiments, the immunogenic composition further comprises an adjuvant. The present invention is not limited to any particular adjuvant and any one or more adjuvants described herein find use in a composition of the invention including but not limited to adjuvants that skew toward a Th1 and/or Th2 type immune responses described herein. In some embodiments, the immunogen comprises a *Streptococcus* product (e.g., including, but not limited to, a protein, peptide, polypeptide, nucleic acid, polysaccharide, or a membrane component derived from the *Streptococcus*). In some embodiments, the immunogen and the nanoemulsion are combined in a single vessel.

In some embodiments, the present invention provides a method of inducing an immune response to *Streptococcus* (e.g., *Streptococcus pneumoniae*) in a subject comprising: providing a subject and an immunogenic composition comprising a nanoemulsion and an immunogen, wherein the immunogen comprises a *Streptococcus* (e.g., *Streptococcus pneumoniae*) antigen and administering the composition to the subject under conditions such that the subject generates a *Streptococcus* (e.g., *Streptococcus pneumoniae*) specific immune response. The present invention is not limited by the route chosen for administration of a composition of the present invention. In some preferred embodiments, administering the immunogenic composition comprises contacting a mucosal surface of the subject with the composition. In some embodiments, the mucosal surface comprises nasal mucosa. In some embodiments, inducing an immune response induces immunity to *Streptococcus* (e.g., *Streptococcus pneumoniae*) in the subject. In some embodiments, the immunity comprises systemic immunity. In some embodiments, the immunity comprises mucosal immunity. In some embodiments, the immune response comprises altered (e.g., enhanced) cytokine expression in the subject. In some embodiments, the immune response comprises an IgG response (e.g., a systemic IgG response) to the *Streptococcus* (e.g., *Streptococcus pneumoniae*) in the subject. In some embodiments, the *Streptococcus* (e.g., *Streptococcus pneumoniae*) antigenic composition is administered to the subject under conditions such that between about $10^5$ and $10^8$ colony forming units (CFU) of *Streptococcus* (e.g., *Streptococcus pneumoniae*) is present in a dose administered to the subject, although greater (e.g., about $10^9$, $10^{10}$, $10^{11}$, $10^{12}$, or more) and lesser (e.g., about $10^4$, $10^3$, $10^2$ or fewer) CFU of *Streptococcus* (e.g., *Streptococcus pneumoniae*) (e.g., killed whole *Streptococcus pneumoniae*) may also be utilized. In some embodiments, a nanoemulsion solution is utilized to inactivate the *Streptococcus* (e.g., *Streptococcus pneumoniae*). In some embodiments, the nanoemulsion comprises $W_{80}5EC$. In some embodiments, the immunity protects the subject from displaying signs or symptoms of disease caused by *Streptococcus* (e.g., *Streptococcus pneumoniae*). In some embodiments, the immunity protects the subject from challenge with a subsequent exposure to live *Streptococcus* (e.g., *Streptococcus pneumoniae*). In some embodiments, the composition further comprises an adjuvant. In some embodiments, the subject is a human. In some embodiments, inducing an immune response induces immunity to the *Streptococcus* (e.g., *Streptococcus pneumoniae*) in the subject. In some embodiments, inducing immunity to *Streptococcus* (e.g., *Streptococcus pneumoniae*) comprises systemic immunity. In some embodiments, immunity comprises mucosal immunity. In some embodiments, the immune response comprises altered (e.g., increased) cytokine expression in the subject. In some embodiments, the immune response comprises a systemic IgG response to the immunogen. In some embodiments, the immune response comprises a mucosal IgA response to the immunogen. In some embodiments, each dose comprises an amount of *Streptococcus* (e.g., *Streptococcus pneumoniae*) antigen sufficient to generate an immune response to the *Streptococcus* (e.g., *Streptococcus pneumoniae*). An effective amount of the *Streptococcus* (e.g., *Streptococcus pneumoniae*) antigen is a dose that need not be quantified, as long as the amount of *Streptococcus* (e.g., *Streptococcus pneumoniae*) antigen generates an immune response in a subject when administered to the subject. In some embodiments, when a nanoemulsion of the present invention is utilized to inactivate *Streptococcus* (e.g., *Streptococcus pneumoniae*), it is expected that each dose (e.g., administered to a subject to induce and immune response)) comprises between 10 and $10^{10}$ CFU of *Streptococcus* (e.g., *Streptococcus pneumoniae*) per dose; in some embodiments, each dose comprises between $10^5$ and $10^8$ CFU of *Streptococcus* (e.g., *Streptococcus pneumoniae*) per dose; in some embodiments, each dose comprises between $10^3$ and $10^5$ CFU of *Streptococcus* (e.g., *Streptococcus pneumoniae*) per dose; in some embodiments, each dose comprises between $10^5$ and $10^8$ CFU of *Streptococcus* (e.g., *Streptococcus pneumoniae*) per dose; in some embodiments, each dose comprises $10^5$ CFU of *Streptococcus* (e.g., *Streptococcus pneumoniae*) per dose; in some embodiments, each dose comprises $10^6$ CFU of *Streptococcus* (e.g., *Streptococcus pneumoniae*) per dose; and in some embodiments, each dose comprises $10^7$ CFU of *Streptococcus* (e.g., *Streptococcus pneumoniae*) per dose. In some embodiments, each dose comprises more than $10^8$ CFU of *Streptococcus* (e.g., *Streptococcus pneumoniae*) per dose. In some preferred embodiments, each dose comprises $10^8$ CFU of *Streptococcus* (e.g., *Streptococcus pneumoniae*) per dose.

The present invention is not limited to any specific nanoemulsion composition. Indeed, a variety of nanoemulsion compositions are described herein that find use in the present invention. Similarly, the present invention is not limited to a particular oil present in the nanoemulsion. A variety of oils are contemplated, including, but not limited to, soybean, avocado, squalene, olive, canola, corn, rapeseed, safflower, sunflower, fish, flavor, and water insoluble vitamins. The present invention is also not limited to a particular solvent. A variety of solvents are contemplated including, but not limited to, an alcohol (e.g., including, but not limited to, methanol, ethanol, propanol, and octanol), glycerol, polyethylene glycol, and an organic phosphate based solvent. Nanoemulsion components including oils, solvents and others are described in further detail below.

In some embodiments, the emulsion further comprises a surfactant. The present invention is not limited to a particular surfactant. A variety of surfactants are contemplated including, but not limited to, nonionic and ionic surfactants (e.g., TRITON X-100; TWEEN 20; and TYLOXAPOL).

In certain embodiments, the emulsion further comprises a cationic halogen containing compound. The present invention is not limited to a particular cationic halogen containing compound. A variety of cationic halogen containing compounds are contemplated including, but not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, and tetradecyltrimethylammonium halides. The present invention is also not limited to a particular halide. A variety of halides are contemplated including, but not limited to, halide selected from the group consisting of chloride, fluoride, bromide, and iodide.

In still further embodiments, the emulsion further comprises a quaternary ammonium containing compound. The present invention is not limited to a particular quaternary ammonium containing compound. A variety of quaternary ammonium containing compounds are contemplated including, but not limited to, Alkyl dimethyl benzyl ammonium chloride,
dialkyl dimethyl ammonium chloride, n-Alkyl dimethyl benzyl ammonium chloride, n-Alkyl dimethyl ethylbenzyl ammonium chloride, Dialkyl dimethyl ammonium chloride, and n-Alkyl dimethyl benzyl ammonium chloride.

In some embodiments, the present invention provides a vaccine comprising an immunogenic composition comprising *Streptococcus* (e.g., *Streptococcus pneumoniae*) antigen (e.g., killed and/or inactivated whole cell *Streptococcus* (e.g., *Streptococcus pneumoniae*)). In some embodiments, the invention provides a kit comprising a vaccine, the vaccine comprising a nanoemulsion and immunogenic composition comprising *Streptococcus* (e.g., *Streptococcus pneumoniae*) antigen, the emulsion comprising an aqueous phase, an oil phase, and a solvent. In some embodiments, the kit further comprises instructions for using the kit for vaccinating a subject against the *Streptococcus* (e.g., *Streptococcus pneumoniae*).

In still further embodiments, the present invention provides a method of inducing immunity to one or more bacteria of the genus *Streptococcus* (e.g., *Streptococcus pneumoniae*) comprising providing an emulsion comprising an aqueous phase, an oil phase, and a solvent; and one or more *Streptococcus* (e.g., *Streptococcus pneumoniae*) antigens; combining the emulsion with the one or more *Streptococcus* (e.g., *Streptococcus pneumoniae*) antigens to generate a vaccine composition; and administering the vaccine composition to a subject. In some embodiments, administering comprises contacting the vaccine composition with a mucosal surface of the subject. For example, in some preferred embodiments, administering comprises intranasal administration. In some preferred embodiments, the administering occurs under conditions such that the subject generates immunity to the one or more bacteria of the genus *Streptococcus* (e.g., *Streptococcus pneumoniae*) (e.g., via generating humoral immune responses to the one or more antigens).

The present invention is not limited by the nature of the immune response generated (e.g., post administration of an immunogenic composition. Indeed, a variety of immune responses may be generated and measured in a subject administered a composition of the present invention including, but not limited to, activation, proliferation or differentiation of cells of the immune system (e.g., B cells, T cells, dendritic cells, antigen presenting cells (APCs), macrophages, natural killer (NK) cells, etc.); up-regulated or down-regulated expression of markers and cytokines; stimulation of IgA, IgM, and/or IgG titers; splenomegaly (e.g., increased spleen cellularity); hyperplasia, mixed cellular infiltrates in various organs, and/or other responses (e.g., of cells) of the immune system that can be assessed with respect to immune stimulation known in the art. In some embodiments, administering comprises contacting a mucosal surface of the subject with the composition. The present invention is not limited by the mucosal surface contacted. In some preferred embodiments, the mucosal surface comprises nasal mucosa. In some embodiments, administering comprises parenteral administration. The present invention is not limited by the route chosen for administration of a composition of the present invention. In some embodiments, inducing an immune response induces immunity to the one or more bacteria of the genus *Streptococcus* (e.g., *Streptococcus pneumoniae*) in the subject. In some embodiments, the immunity comprises systemic immunity. In some embodiments, the immunity comprises mucosal immunity. In some embodiments, the immune response comprises altered (e.g., increased) cytokine expression in the subject. In some embodiments, the immune response comprises a systemic IgG response. In some embodiments, the immune response comprises a mucosal IgA response. In some embodiments, the composition comprises a 15% nanoemulsion solution. However, the present invention is not limited to this amount (e.g., percentage) of nanoemusion. For example, in some embodiments, a composition comprises less than 10% nanoemulsion (e.g., 9%, 8%, 7%, 6%, 5%, 4%, 3%, 2% or 1%). In some embodiments, a composition comprises more than 10% nanoemulsion (e.g., 15%, 20%, 25%, 30%, 35%, 40%. 45%, 50%, 60% or more). In some embodiments, a composition of the present invention comprises any of the nanoemulsions described herein. In some embodiments, the nanoemulsion comprises $W_{20}5EC$. In some preferred embodiments, the nanoemulsion comprises $W_{80}5EC$. In some embodiments, the nanoemulsion is X8P. In some embodiments, immunity protects the subject from displaying signs or symptoms of disease caused by a bacteria of the genus *Streptococcus* (e.g., *Streptococcus pneumoniae*). In some embodiments, immunity protects the subject from challenge with a subsequent exposure to a live bacterium of the genus *Streptococcus* (e.g., *Streptococcus pneumoniae*). In some embodiments, the composition further comprises an adjuvant. The present invention is not limited by the type of adjuvant utilized. In some embodiments, the adjuvant is cholera toxin (CT). In some embodiments, the adjuvant is monophosphoryl lipid A and/or a CpG oligonucleotide. A number of other adjuvants that find use in the present invention are described herein. In some embodiments, the subject is a human. In some embodiments, the immunity protects the subject from displaying signs or symptoms of a infection with a bacteria of the genus *Streptococcus* (e.g., *Streptococcus pneumoniae*). In some embodiments, immunity reduces the risk of infection, disease, and/or sickness upon one or more exposures to a bacteria of the genus *Streptococcus* (e.g., *Streptococcus pneumoniae*).

DESCRIPTION OF THE DRAWINGS

The following figures form part of the present specification and are included to further demonstrate certain aspects and embodiments of the present invention. The invention may be better understood by reference to one or more of these figures in combination with the description of specific embodiments presented herein.

FIG. 1 shows the preparation of various single dose formulations of vaccines using stock WCPAg.

GENERAL DESCRIPTION OF THE INVENTION

Figure 2:
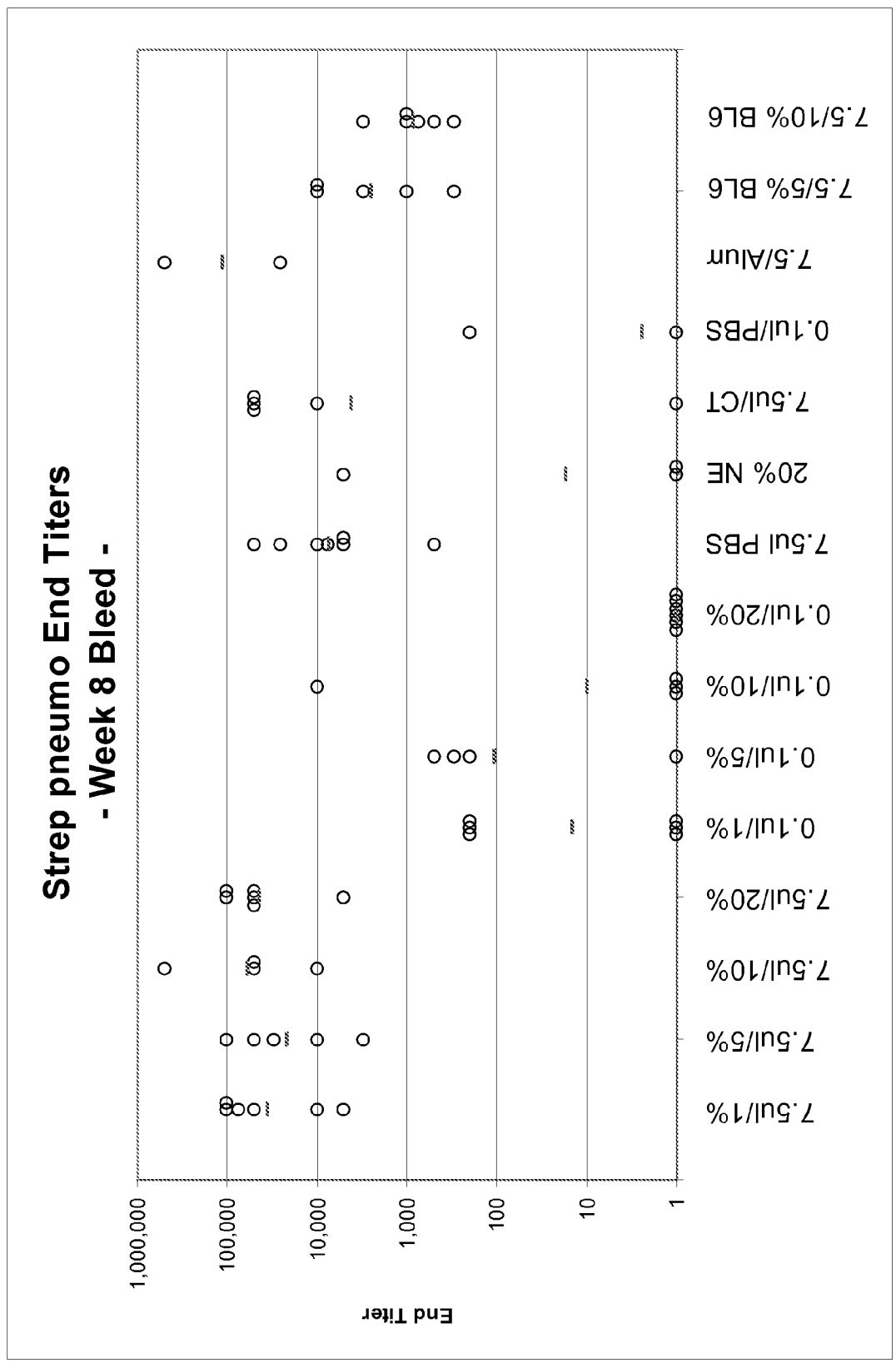
FIG. 2 shows the distribution of anti-*S. pneumoniae* antibody titers at 8 weeks after two vaccinations.

The present invention provides methods and compositions for the stimulation of immune responses. In particular, the present invention provides immunogenic nanoemulsion compositions and methods of using the same for the induction of immune responses (e.g., innate and/or adaptive immune responses (e.g., for generation of host immunity against a bacterial species of the genus *Streptococcus* (e.g., *Streptococcus pneumoniae*))). Compositions and methods of the present invention find use in, among other things, clinical (e.g. therapeutic and preventative medicine (e.g., vaccination)) and research applications.

Although an understanding of the mechanism is not necessary to practice the present invention and the present invention is not limited to any particular mechanism of action, in some embodiments, nanoemulsion (NE) compositions stabilize and/or preserve (e.g., for antigen presentation) important antigenic epitopes (e.g., recognizable by a subject's immune system) of a bacteria of the genus *Streptococcus* (e.g., *Streptococcus pneumoniae*)) (e.g., stabilize and/or preserve hydrophobic and/hydrophilic components in the oil and water interface of the emulsion (e.g., thereby providing one or more immunogens (e.g., stabilized antigens) against which a subject can mount an immune response). In other embodiments, because NE formulations penetrate the mucosa through pores, they may carry antigens/immunogens to the submucosal location of dendritic cells (e.g., thereby initiating and/or stimulating an immune response). Although an understanding of the mechanism is not necessary to practice the present invention and the present invention is not limited to any particular mechanism of action, in some embodiments, combining a NE and *Streptococcus* (e.g., *Streptococcus pneumoniae*)) antigen stabilizes and/or preserves *Streptococcus* (e.g., *Streptococcus pneumoniae*)) immunogens and provides a proper immunogenic material for generation of an immune response. Dendritic cells avidly phagocytose nanoemulsion (NE) oil droplets and this provides one mechanism to internalize immunogens (e.g., antigenic proteins or peptide fragments thereof of *Streptococcus* (e.g., *Streptococcus pneumoniae*) for antigen presentation. While other vaccines rely on inflammatory toxins or other immune stimuli for adjuvant activity (See, e.g., Holmgren and Czerkinsky, Nature Med. 2005, 11; 45-53), NEs have not been shown to be inflammatory when placed on the skin or mucous membranes in studies on animals and in humans. Thus, although an understanding of the mechanism is not necessary to practice the present invention and the present invention is not limited to any particular mechanism of action, in some embodiments, a composition comprising a NE of the present invention (e.g., a composition comprising NE and one or more *Streptococcus* (e.g., *Streptococcus pneumoniae*)) antigens may act as a "physical" adjuvant (e.g., that transports and/or presents immunogenic compositions (e.g., peptides and/or antigens of *Streptococcus* (e.g., *Streptococcus pneumoniae*)) to the immune system. In some embodiments, mucosal administration of a composition of the present invention generates mucosal (e.g., signs of mucosal immunity (e.g., generation of IgA antibody titers)) as well as systemic immunity.

Both cellular and humoral immunity play a role in protection against multiple pathogens and both can be induced with the NE formulations of the present invention. In some embodiments, administration (e.g., mucosal administration) of a composition of the present invention to a subject results in the induction of both humoral (e.g., development of specific antibodies) and cellular (e.g., cytotoxic T lymphocyte) immune responses (e.g., against *Streptococcus* (e.g., *Streptococcus pneumoniae*)). In some embodiments, a composition of the present invention (e.g., immunogenic composition comprising NE and *Streptococcus* (e.g., *Streptococcus pneumoniae*)) antigen is used as a vaccine (e.g., an RSV vaccine).

DEFINITIONS

To facilitate an understanding of the present invention, a number of terms and phrases are defined below:

As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc.

As used herein, the term *Streptococcus* refers to a genus of spherical Gram positive bacteria belonging to the phylum Firmicutes and the lactic acid bacteria group. In general, Streptococci are oxidase-negative and catalase-negative, and many are facultative anaerobes. In general, individual species of *Streptococcus* are classified based on their hemolytic properties. Alpha hemolysis is caused by a reduction of iron in hemoglobin, giving it a greenish color on blood agar. Beta-only hemolysis is complete rupture of red blood cells, giving distinct, wide, clear areas around bacterial colonies on blood agar. Other streptococci are labeled as gamma hemolytic.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered) the compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered or who has been administered one or more compositions of the present invention (e.g., a composition for inducing an immune response).

As used herein, the terms "inactivating," "inactivation" and grammatical equivalents, when used in reference to a microorganism (e.g., a pathogen (e.g., a bacterium or a virus)), refer to the killing, elimination, neutralization and/or reducing of the capacity of the microorganism (e.g., a pathogen (e.g., a bacterium or a virus)) to infect and/or cause a pathological response and/or disease in a host. For example, in some embodiments, the present invention provides a composition comprising nanoemulsion (NE)-inactivated Staphylococci. Accordingly, as referred to herein, compositions comprising "NE-inactivated Staphylococci," "NE-killed Staphylococci," NE-neutralized Staphylococci" or grammatical equivalents refer to compositions that, when administered to a subject, are characterized by the absence of, or significantly reduced presence of, Staphylococci replication (e.g., over a period of time (e.g., over a period of days, weeks, months, or longer)) within the host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium or bacterial spore). In preferred embodiments of the present invention, the presence of a lysogenic and a fusigenic agent in the same composition produces an enhanced inactivating effect compared to either agent alone. Methods and compositions (e.g., for inducing an immune response (e.g., used as a vaccine) using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in some embodiments, the nanoemulsions comprise an oil phase having droplets with a mean particle size of approximately 0.1 to 5 microns (e.g., about 150, 200, 250, 300, 350, 400, 450, 500 nm or larger in diameter), although smaller and larger particle sizes are contemplated. The terms "emulsion" and "nanoemulsion" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion inactivates the microorganism or pathogenic agent, if present. The present invention is not limited by the amount or type of nanoemulsion used for microorganism inactivation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion (e.g., sufficient for inactivating the microorganism (e.g., virus inactivation)) and microorganisms (e.g., sufficient to provide an antigenic composition (e.g., a composition capable of inducing an immune response)) are contemplated in the present invention including, but not limited to, those described herein.

The term "surfactant" refers to any molecule having both a polar head group, which energetically prefers solvation by water, and a hydrophobic tail that is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., *Meyers, Surfactant Science and Technology*, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis(oxyethylenenitrilo)tetraacetic acid (EGTA), and the like) and certain biological agents (e.g., bovine serum albumin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to a microorganism (e.g., pathogen) capable of causing disease). In preferred embodiments of the invention, the composition comprises a nanoemulsion and an immunogen. In further preferred embodiments, the composition comprising a nanoemulsion and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, a composition comprising a nanoemulsion and an immunogen is administered to a subject as a vaccine (e.g., to prevent or attenuate a disease (e.g., by providing to the subject total or partial immunity against the disease or the total or partial attenuation (e.g., suppression) of a sign, symptom or condition of the disease.

As used herein, the term "adjuvant" refers to any substance that can stimulate an immune response (e.g., a mucosal immune response). Some adjuvants can cause activation of a cell of the immune system (e.g., an adjuvant can cause an immune cell to produce and secrete a cytokine). Examples of adjuvants that can cause activation of a cell of the immune system include, but are not limited to, the nanoemulsion formulations described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); cholera toxin (CT), and *Leishmania* elongation factor (a purified *Leishmania* protein; Corixa Corporation, Seattle, Wash.). Traditional adjuvants are well known in the art and include, for example, aluminum phosphate or hydroxide salts ("alum"). In some embodiments, compositions of the present invention (e.g., comprising HIV or an immunogenic epitope thereof (e.g., gp120)) are administered with one or more adjuvants (e.g., to skew the immune response towards a Th1 and/or Th2 type response).

As used herein, the term "an amount effective to induce an immune response" (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the terms "toll receptors" and "TLRs" refer to a class of receptors (e.g., TLR1, TLR2, TLR3, TLR4, TLR5, TLR6, TLR7, TLR8, TLR9, TLR10, TLR 11) that recognize special patterns of pathogens, termed pathogen-associated molecular patterns (See, e.g., Janeway and Medzhitov, (2002) Annu. Rev. Immunol. 20, 197-216). These receptors are expressed in innate immune cells (e.g., neutrophils, monocytes, macrophages, dendritic cells) and in other types of cells such as endothelial cells. Their ligands include bacterial products such as LPS, peptidoglycans, lipopeptides, and CpG DNA. TLRs are receptors that bind to exogenous ligands and mediate innate immune responses leading to the elimination of invading microbes. The TLR-triggered signaling pathway leads to activation of transcription factors including NFkB, which is important for the induced expression of proinflammatory cytokines and chemokines. TLRs also interact with each other. For example, TLR2 can form functional heterodimers with TLR1 or TLR6. The TLR2/1 dimer has different ligand binding profile than the TLR2/6 dimer (Ozinsky et al., 2000). In some embodiments, a nanoemulsion adjuvant activates cell signaling through a TLR (e.g., TLR2 and/or TLR4). Thus, methods described herein include a nanoemulsion adjuvant composition (e.g., composition comprising NE adjuvant optionally combined with one or more immunogens (e.g., *Streptococcus* (e.g., *Streptococcus pneumoniae*) antigens) that when administered to a subject, activates one or more TLRs and stimulates an immune response (e.g., innate and/or adaptive/acquired immune response) in a subject. Such an adjuvant can activate TLRs (e.g., TLR2 and/or TLR4) by, for example, interacting with TLRs (e.g., NE adjuvant binding to TLRs) or activating any downstream cellular pathway that occurs upon binding of a ligand to a TLR. NE adjuvants described herein that activate TLRs can also enhance the availability or accessibility of any endogenous or naturally occurring ligand of TLRs. A NE adjuvant that activates one or more TLRs can alter transcription of genes, increase translation of mRNA or increase the activity of proteins that are involved in mediating TLR cellular processes. For example, NE adjuvants described herein that activate one or more TLRs (e.g., TLR2 and/or TLR4) can induce expression of one or more cytokines (e.g., IL-8, IL-12p40, and/or IL-23)

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired/adaptive (e.g., immune responses that are mediated by B and T cells following a previous exposure to antigen (e.g., that exhibit increased specificity and reactivity to the antigen)).

As used herein, the terms "immunogen" and "antigen" refer to an agent (e.g., a microorganism (e.g., bacterium, virus or fungus) and/or portion or component thereof (e.g., a protein antigen)) that is capable of eliciting an immune response in a subject. In preferred embodiments, immunogens elicit immunity against the immunogen (e.g., microorganism (e.g., pathogen or a pathogen product)) when administered in combination with a nanoemulsion of the present invention. As used herein, the term *Streptococcus* antigen refers to a component or product of a bacteria of the genus *Streptococcus* that elicits an immune response when administered to a subject.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response (e.g., a composition comprising a nanoemulsion and an immunogen)) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like.

As used herein, the terms "co-administration" and "co-administering" refer to the administration of at least two agent(s) (e.g., a composition comprising a nanoemulsion and an immunogen and one or more other agents—e.g., an adjuvant) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., microorganisms (e.g., pathogens)) at or near the same time (e.g., when a subject is unlikely to be available for subsequent administration of a second, third, or more composition for inducing an immune response).

As used herein, the term "topically" refers to application of a compositions of the present invention (e.g., a composition comprising a nanoemulsion and an immunogen) to the surface of the skin and/or mucosal cells and tissues (e.g., alveolar, buccal, lingual, masticatory, vaginal or nasal mucosa, and other tissues and cells which line hollow organs or body cavities).

In some embodiments, the compositions of the present invention are administered in the form of topical emulsions, injectable compositions, ingestible solutions, and the like. When the route is topical, the form may be, for example, a spray (e.g., a nasal spray), a cream, or other viscous solution (e.g., a composition comprising a nanoemulsion and an immunogen in polyethylene glycol).

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethyl glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

As used herein, the term "kit" refers to any delivery system for delivering materials. In the context of immunogenic agents (e.g., compositions comprising a nanoemulsion and an immunogen), such delivery systems include systems that allow for the storage, transport, or delivery of immunogenic agents and/or supporting materials (e.g., written instructions for using the materials, etc.) from one location to another. For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion and an immunogen for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

DETAILED DESCRIPTION OF THE INVENTION

*Streptococcus pneumoniae* is a Gram-positive bacterium responsible for considerable morbidity and mortality (particularly in the young and aged), causing invasive diseases such as *pneumoniae*, bacteraemia and meningitis, and diseases associated with colonization, such as acute Otitis media. The rate of pneumococcal *pneumoniae* in the US for persons over 60 years of age is estimated to be 3 to 8 per 100,000. In 20% of cases this leads to bacteraemia, and other manifestations such as meningitis, with a mortality rate close to 30% even with antibiotic treatment.

*Pneumococcus* is encapsulated with a chemically linked polysaccharide which confers serotype specificity. There are 90 known serotypes of pneumococci, and the capsule is the principle virulence determinant for pneumococci, as the capsule not only protects the inner surface of the bacteria from complement, but is itself poorly immunogenic. Polysaccharides are T-independent antigens, and have been shown to not be processed or presented on MHC molecules to interact with T-cells. They can however, stimulate the immune system through an alternate mechanism which involves cross-linking of surface receptors on B cells. It has been documents that protection against invasive pneumococci disease is correlated most strongly with antibody specific for the capsule, and the protection is serotype specific.

*Streptococcus pneumoniae* is the most common cause of invasive bacterial disease and Otitis media in infants and young children. Likewise, the elderly mount poor responses to pneumococcal vaccines (See, e.g., Roghmann et al., (1987), J. Gerontol. 42:265-270], hence the increased incidence of bacterial pneumonia in this population (See, e.g., Verghese and Berk, (1983) Medicine (Baltimore) 62:271-285).

Accordingly, the present invention provides methods and compositions for the stimulation of immune responses. In particular, the present invention provides immunogenic nanoemulsion compositions and methods of using the same for the induction of immune responses (e.g., innate and/or adaptive immune responses (e.g., for generation of host immunity against a bacterial species of the genus *Streptococcus* (e.g., *Streptococcus pneumoniae*))). Compositions and methods of the present invention find use in, among other things, clinical (e.g. therapeutic and preventative medicine (e.g., vaccination)) and research applications.

In some embodiments, the present invention provides nanoemulsion adjuvants and compositions comprising the same (e.g., vaccines) for the stimulation of immune responses (e.g., immunity) against a bacterial species of the genus *Streptococcus* (e.g., *Streptococcus pneumoniae*). In some embodiments, the present invention provides nanoemulsion adjuvant compositions that stimulate and/or elicit immune responses (e.g., innate immune responses and/or adaptive/acquired immune responses) when administered to a subject (e.g., a human subject)). In some embodiments, the present invention provides nanoemulsion adjuvant compositions comprising one or a plurality of *Streptococcus* (e.g., *Streptococcus pneumoniae*)) antigens (e.g., *Streptococcus* components and/or inactivated *Streptococcus*). The present invention is not limited to any particular nanoemulsion or *Streptococcus* (e.g., *Streptococcus pneumoniae*)) antigen. Exemplary immunogenic compositions (e.g., vaccine compositions) and methods of administering the compositions are described in more detail below.

In some embodiments, the present invention provides an immunogenic composition comprising a nanoemulsion and one or more *Streptococcus* antigens (e.g., *Streptococcus pneumoniae* antigens). In some embodiments, the present invention provides a method of inducing an immune response to *Streptococcus* (e.g., *Streptococcus pneumoniae*) in a subject comprising: providing a subject and an immunogenic composition comprising a nanoemulsion and an immunogen, wherein the immunogen comprises a *Streptococcus* (e.g., *Streptococcus pneumoniae*) antigen and administering the composition to the subject under conditions such that the subject generates a *Streptococcus* (e.g., *Streptococcus pneumoniae*) specific immune response. The present invention is not limited by the route chosen for administration of a composition of the present invention. In some preferred embodiments, administering the immunogenic composition comprises contacting a mucosal surface of the subject with the composition. In some embodiments, the mucosal surface comprises nasal mucosa. In some embodiments, inducing an immune response induces immunity to *Streptococcus* (e.g., *Streptococcus pneumoniae*) in the subject.

Experiments were conducted during development of embodiments of the invention to determine if a composition comprising a nanoemulsion (NE) and *Streptococcus pneumoniae* antigen could be utilized to generate an immune response in a subject. Nasal immunization with a whole cell *Streptococcus pneumoniae* antigen (WCPAg) mixed with nanoemulsion was performed and shown to induce an IgG response in a host subject and the ability to eradicate upper respiratory colonization of *S. pneumoniae*.

In particular, as described in Examples 1-4, experiments were conducted to determine whether *S. pneumoniae* mixed with nanoemulsion could produce an immune response. CD-1 and C57/B6 mice were immunized with three intranasal doses of WCPAg ($1\times10^8$ CFU or $1\times10^6$ CFU) (See, e.g., Malley et al., (2001) Infect. Immun. 69, 4870-4873; Malley et al., (2004) Infect. Immun. 72, 4290-4292)) combined with various concentrations of nanoemulsion. Serum antibody titers show that mixing of *Streptococcus* antigen (WCPAg/ $W_{80}5EC$) with nanoemulsion resulted in 10- to 20-fold increase in immune response over the levels obtained without nanoemulsion, and was comparable with the standard intramuscular immunization with alum adjuvant (See FIGS. 3A and 3B).

Figure 4:
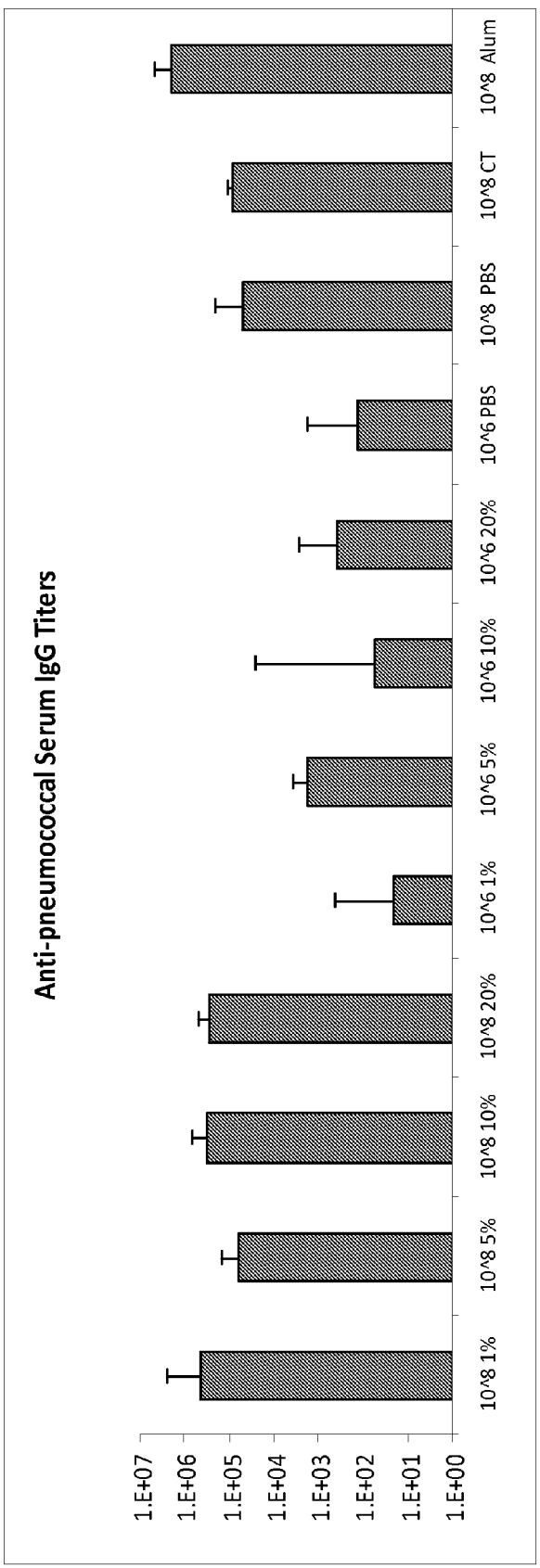
FIG. 4 shows serum anti-*S. pneumoniae* IgG antibodies in CD-1 mice measured at 11 weeks after primary immunization presented as endpoint titters (+/−sd).

To test the protective effect of immunization mice were intranasally infected with *S. pneumoniae*. Analysis of bacteria recovered from the nasal washes 7 days post-colonization indicated protection against pneumococcal colonization and decrease in colonization of the upper respiratory tract in the mice immunized with $10^8$ CFU WCPAg plus nanoemulsion (See FIG. 4).

The efficacy of intranasal WCPAg/$W_{80}5EC$ vaccine was evaluated at antigen doses of 7.5 µL and 0.1 µL in 1, 5, 10 and 20% nanoemulsion (NE). The results indicated that the doses of 7.5 µL, WCPAg in 1, 5, 10, and 20% NE elicited an immune response similar to that of the 7.5 µL, WCPAg+Alum group. Mucosal vaccination with 7.5 µL WCPAg in 1, 5, 10, and 20% NE produced an immune response greater than $1\times10^5$ mean IgG titers after three vaccinations. (See, e.g., Examples 2-4). Additionally, after challenging the mice with $1\times10^5$ colony forming units (CFU) *S. pneumoniae*, there was a marked reduction in carriage in the 7.5 µL, WCPAg/NE and 7.5 µL+Alum groups versus control groups (See FIG. 4). Complete blood counts (white blood cells, neutrophils and monocytes) showed no abnormalities within any of the groups.

Accordingly, in some embodiments, the present invention provides that administration (e.g., nasal administration) of a composition comprising nanoemulsion and *S. pneumoniae* antigen (e.g., whole cell *S. pneumoniae*) to a subject produces immunity toward *S. pneumoniae* in the subject thereby protecting the subject against pneumococcal infection. In some embodiments, compositions and method of the present invention provide Streptococci (e.g., *S. pneumoniae*) specific protective immune responses in a subject (e.g., similar to and/or greater than conventional Streptococci (e.g., *S. pneumoniae*) vaccines (e.g., alum-adjuvanted vaccines))).

The present invention is not limited by the type of bacteria of the genus Streptococci utilized in the immunogenic compositions and methods of using the same of the invention. In some embodiments, the bacteria is a pathogen. In some embodiments, the pathogen is a *Streptococcus* species responsible for strep throat, meningitis, bacterial pneumonia, endocarditis, erysipelas and/or necrotizing fasciitis. A variety of *Streptococcus* species find use in the compositions and methods of the invention including *S. pneumoniae*, *S. mutans*, *S. mitis*, *S. sanguinis*, *S. salivarius*, *S. viridans*, *S. salivarius* ssp. *thermophilus*, *S. constellatus*, *S. pyogenes*, *S. agalactiae*, *S. zooepidemicus*, *Streptococcus bovis* and *Streptococcus equines*, *Streptococcus canis*, as well as former Group D Streptococci including *S. faecalis*, *S. faecium*, *S. durans*, and *S. avium*.

In some preferred embodiments, the bacteria of the genus Streptococci is *S. pneumoniae*. In some embodiments, an immunogenic composition comprising a nanoemulsion and *S. pneumoniae* antigen may comprise antigens (e.g., polysaccharide, protein, killed whole cells (e.g., conjugated or non-conjugated antigens)), wherein the antigens are derived from multiple (e.g., at least 2, 3, 5, 7, 10, 15, 20, 30, 40, 50, 60, 70, 80 or more) serotypes of *S. pneumoniae*. The number of *S. pneumoniae* antigens utilized can range from 10 different serotypes to about 20 different serotypes. In another embodiment of the invention, the vaccine may comprise conjugated *S. pneumoniae* saccharides and unconjugated *S. pneumoniae* saccharides. For example, the invention may comprise 10 conjugated serotypes and 10 unconjugated saccharides. In some embodiments, an immunogenic composition comprising a nanoemulsion and *S. pneumoniae* antigen may comprise

*S. pneumoniae* antigen (e.g., whole cell, polysaccharide, protein, etc.) from every known and/or isolated serotype.

In some embodiments, an immunogenic composition comprising a nanoemulsion and *S. pneumoniae* antigen comprises *S. pneumoniae* antigen (e.g., polysaccharide, protein, killed whole cells) selected from the following serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F, although it is appreciated other serotypes could be substituted depending on the age of the recipient receiving the vaccine and the geographical location where the vaccine will be administered. In some embodiments, a 10-valent vaccine refers to a composition comprising a nanoemulsion and *S. pneumoniae* antigen, wherein the *S. pneumoniae* antigen comprises antigen (e.g., polysaccharide, protein, killed whole cells) from 10 *S. pneumoniae* serotypes (e.g., serotypes 1, 4, 5, 6B, 7F, 9V, 14, 18C, 19F and 23F). In some embodiments, a 1-valent vaccine refers to a composition comprising a nanoemulsion and *S. pneumoniae* antigen, wherein the *S. pneumoniae* antigen comprises antigen (e.g., polysaccharide, protein, killed whole cells) from one *S. pneumoniae* serotype 3. In some embodiments, certain immunogenic compositions comprising a nanoemulsion and *S. pneumoniae* antigen comprise *S. pneumoniae* antigen (e.g., polysaccharide, protein, killed whole cells) from a variety of serotypes associated with pediatric infection (e.g., may comprise serotypes 6A and 19A, or 6A and 22F, or 19A and 22F, or 6A and 15B, or 19A and 15B, or 22F and 15B). In some embodiments, certain immunogenic compositions comprising a nanoemulsion and *S. pneumoniae* antigen comprise *S. pneumoniae* antigen (e.g., polysaccharide, protein, killed whole cells) from a variety of serotypes associated with infection of the elderly (e.g., may comprise the serotypes 6A and 19A, or 6A and 22F, or 19A and 22F, or 6A and 15B, or 19A and 15B, or 22F and 15B, supplemented with serotypes 19A and 22F, 8 and 12F, or 8 and 15B, or 8 and 19A, or 8 and 22F, or 12F and 15B, or 12F and 19A, or 12F and 22F, or 15B and 19A, or 15B and 22F).

In some embodiments, certain immunogenic compositions comprising a nanoemulsion and *S. pneumoniae* antigen comprise *S. pneumoniae* antigen (e.g., polysaccharide, protein, killed whole cells) from a variety of serotypes comprising serotypes 1, 2, 3, 4, 5, 6B, 7F, 8, 9N, 9V, 10A, 11A, 12F, 14, 15B, 17F, 18C, 19A, 19F, 20, 22F, 23F and 33F.

In some embodiments, an immunogenic composition comprising a nanoemulsion and *Streptococcus* (e.g., *Streptococcus pneumoniae*) antigen comprises protein D (PD) from *Haemophilus influenzae* (see e.g. EP 0594610). *Haemophilus influenzae* is a key causative organism of otitis media (e.g., thereby protecting against *Haemophilus influenzae* related otitis media). In one embodiment, the vaccine composition comprises protein D. In one aspect, PD is present as a carrier protein. In another aspect, protein D is present in the vaccine composition as a free protein. In a further aspect, protein D is present both as a carrier protein and as free protein. Protein D may be used as a full length protein or as a fragment (See, e.g., WO0056360).

In some embodiments, an immunogenic composition comprising a nanoemulsion and *Streptococcus* (e.g., *Streptococcus pneumoniae*) antigen comprises one, two or more different types of carrier protein (e.g., that act as carriers for proteins, saccharides, etc.). For example, in one embodiment, two or more different saccharides or proteins may be conjugated to the same carrier protein, either to the same molecule of carrier protein or to different molecules of the same carrier protein. Carrier proteins may be TT, DT, CRM197, fragment C of TT, PhtD, PhtBE or PhtDE fusions (particularly those described in WO 01/98334 and WO 03/54007), detoxified pneumolysin and protein D. In some embodiments, a carrier protein present in a composition comprising a nanoemulsion and *Streptococcus* (e.g., *Streptococcus pneumoniae*) antigen is a member of the polyhistidine triad family (Pht) proteins, fragments or fusion proteins thereof. The PhtA, PhtB, PhtD or PhtE proteins may have an amino acid sequence sharing 80%, 85%, 90%, 95%, 98%, 99% or 100% identity with a sequence disclosed in WO 00/37105 or WO 00/39299 (e.g. with amino acid sequence 1-838 or 21-838 of SEQ ID NO: 4 of WO 00/37105 for PhtD). For example, fusion proteins are composed of full length or fragments of 2, 3 or 4 of PhtA, PhtB, PhtD, PhtE. Examples of fusion proteins are PhtA/B, PhtA/D, PhtA/E, PhtB/A, PhtB/D, PhtB/E. PhtD/A. PhtD/B, PhtD/E, PhtE/A, PhtE/B and PhtE/D, wherein the proteins are linked with the first mentioned at the N-terminus (see for example WO01/98334). Carriers may comprise histidine triad motif (s) and/or coiled coil regions. A histidine triad motif is the portion of polypeptide that has the sequence HxxHxH where H is histidine and x is an amino acid other than histidine. A coiled coil region is a region predicted by "Coils" algorithm Lupus, A et al (1991) Science 252; 1162-1164.

Examples of carrier proteins which may be used in the present invention are DT (Diphtheria toxoid), TT (tetanus toxoid) or fragment C of TT, DT CRM197 (a DT mutant) other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711, pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE and fusions of Pht proteins for example PhtDE fusions, PhtBE fusions (WO 01/98334 and WO 03/54007), (Pht A-E are described in more detail below) OMPC (meningococcal outer membrane protein—usually extracted from *N. meningitidis* serogroup B-EP0372501), PorB (from *N. meningitidis*), PD (*Haemophilus influenzae* protein D—see, e.g., EP 0 594 610 B), or immunologically functional equivalents thereof, synthetic peptides (EP0378881, EPO427347), heat shock proteins (WO 93/17712, WO 94/03208), pertussis proteins (WO 98/58668, EPO471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761).

Generation of Antibodies

An immunogenic composition comprising a nanoemulsion and *Streptococcus* (e.g., *Streptococcus pneumoniae*) antigen can be used to immunize a mammal, such as a mouse, rat, rabbit, guinea pig, monkey, or human, to produce polyclonal antibodies. If desired, a *Streptococcus* (e.g., *Streptococcus pneumoniae*) antigen can be conjugated to a carrier protein, such as bovine serum albumin, thyroglobulin, keyhole limpet hemocyanin or other carrier described herein. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, nanoemulsions described herein, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to a *Streptococcus* (e.g., *Streptococcus pneumoniae*) antigen can be prepared using any technique which provides for the production of antibody molecules by continuous cell lines in culture. These techniques include, but are not limited to, the hybridoma technique, the human B cell hybridoma technique, and the EBV hybridoma technique (See, e.g., Kohler et al., Nature 256, 495 497, 1985; Kozbor et al., J. Immunol. Methods 81, 3142, 1985; Cote et al., Proc. Natl. Acad. Sci. 80, 2026 2030, 1983; Cole et al., Mol. Cell. Biol. 62, 109 120, 1984).

In addition, techniques developed for the production of "chimeric antibodies," the splicing of mouse antibody genes to human antibody genes to obtain a molecule with appropriate antigen specificity and biological activity, can be used (See, e.g., Morrison et al., Proc. Natl. Acad. Sci. 81, 68516855, 1984; Neuberger et al., Nature 312, 604 608, 1984; Takeda et al., Nature 314, 452 454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (See, e.g., Burton, Proc. Natl. Acad. Sci. 88, 11120 23, 1991).

Single-chain antibodies also can be constructed using a DNA amplification method, such as PCR, using hybridoma cDNA as a template (See, e.g., Thirion et al., 1996, Eur. J. Cancer Prey. 5, 507-11). Single-chain antibodies can be mono- or bispecific, and can be bivalent or tetravalent. Construction of tetravalent, bispecific single-chain antibodies is taught, for example, in Coloma & Morrison, 1997, Nat. Biotechnol. 15, 159-63. Construction of bivalent, bispecific single-chain antibodies is taught, for example, in Mallender & Voss, 1994, J. Biol. Chem. 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (See, e.g., Verhaar et al., 1995, Int. J. Cancer 61, 497-501; Nicholls et al., 1993, J. Immunol. Meth. 165, 81-91).

Antibodies which specifically bind to a particular antigen also can be produced by inducing in vivo production in the lymphocyte population or by screening immunoglobulin libraries or panels of highly specific binding reagents as disclosed in the literature (See, e.g., Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared. Antibodies can be purified by methods well known in the art. For example, antibodies can be affinity purified by passage over a column to which the relevant antigen is bound. The bound antibodies can then be eluted from the column using a buffer with a high salt concentration.

Nanoemulsions

The present invention is not limited by the type of nanoemulsion adjuvant utilized (e.g., for respiratory administration). Indeed, a variety of nanoemulsion adjuvants are contemplated to be useful in the present invention.

For example, in some embodiments, a nanoemulsion comprises (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweeteners, bulking agents, and the like) and pharmaceutically acceptable compounds (e.g., carriers). Certain exemplary embodiments of the various compounds contemplated for use in the compositions of the present invention are presented below. Unless described otherwise, nanoemulsions are described in undiluted form.

Nanoemulsion adjuvant compositions of the present invention are not limited to any particular nanoemulsion. Any number of suitable nanoemulsion compositions may be utilized in the vaccine compositions of the present invention, including, but not limited to, those disclosed in Hamouda et al., J. Infect Dis., 180:1939 (1999); Hamouda and Baker, J. Appl. Microbiol., 89:397 (2000); and Donovan et al., Antivir. Chem. Chemother., 11:41 (2000). Preferred nanoemulsions of the present invention are those that are non-toxic to animals. In preferred embodiments, nanoemulsions utilized in the methods of the present invention are stable, and do not decompose even after long storage periods (e.g., one or more years). Additionally, preferred emulsions maintain stability even after exposure to high temperature and freezing. This is especially useful if they are to be applied in extreme conditions (e.g., extreme heat or cold). Some embodiments of the present invention employ an oil phase containing ethanol.

For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Exemplary Formulations

The following description provides a number of exemplary emulsions including formulations for compositions BCTP and $X_8W_{60}PC$. BCTP comprises a water-in oil nanoemulsion, in which the oil phase was made from soybean oil, tri-n-butyl phosphate, and TRITON X-100 in 80% water. $X_8W_{60}PC$ comprises a mixture of equal volumes of BCTP with $W_{80}8P$. $W_{80}8P$ is a liposome-like compound made of glycerol monostearate, refined oya sterols (e.g., GENEROL sterols), TWEEN 60, soybean oil, a cationic ion halogen-containing CPC and peppermint oil. The GENEROL family are a group of a polyethoxylated soya sterols (Henkel Corporation, Ambler, Pa.). Exemplary emulsion formulations useful in the present invention are provided in Table 1. These particular formulations may be found in U.S. Pat. No. 5,700,679 (NN); U.S. Pat. Nos. 5,618,840; 5,549,901 ($W_{80}8P$); and U.S. Pat. No. 5,547,677, each of which is hereby incorporated by reference in their entireties. Certain other emulsion formulations are presented U.S. patent application Ser. No. 10/669,865, hereby incorporated by reference in its entirety.

The $X_8W_{60}PC$ emulsion is manufactured by first making the $W_{80}8P$ emulsion and BCTP emulsions separately. A mixture of these two emulsions is then re-emulsified to produce a fresh emulsion composition termed $X_8W_{60}PC$. Methods of producing such emulsions are described in U.S. Pat. Nos. 5,103,497 and 4,895,452 (each of which is herein incorporated by reference in their entireties).

TABLE 1

| | Oil Phase Formula | Water to Oil Phase Ratio (Vol/Vol) |
|---|---|---|
| BCTP | 1 vol. Tri(N-butyl)phosphate<br>1 vol. TRITON X-100<br>8 vol. Soybean oil | 4:1 |
| NN | 86.5 g Glycerol monooleate<br>60.1 ml Nonoxynol-9<br>24.2 g GENEROL 122<br>3.27 g Cetylpyridinium chloride<br>554 g Soybean oil | 3:1 |
| $W_{80}8P$ | 86.5 g Glycerol monooleate<br>21.2 g Polysorbate 60<br>24.2 g GENEROL 122<br>3.27 g Cetylpyddinium chloride<br>4 ml Peppermint oil<br>554 g Soybean oil | 3.2:1 |
| SS | 86.5 g Glycerol monooleate<br>21.2 g Polysorbate 60<br>24.2 g GENEROL 122<br>3.27 g Cetylpyridinium chloride<br>554 g Soybean oil | 3.2:1<br>(1% bismuth in water) |

The compositions listed above are only exemplary and those of skill in the art will be able to alter the amounts of the components to arrive at a nanoemulsion composition suitable for the purposes of the present invention. Those skilled in the art will understand that the ratio of oil phase to water as well as the individual oil carrier, surfactant CPC and organic phosphate buffer, components of each composition may vary.

Although certain compositions comprising BCTP have a water to oil ratio of 4:1, it is understood that the BCTP may be formulated to have more or less of a water phase. For example, in some embodiments, there is 3, 4, 5, 6, 7, 8, 9, 10, or more parts of the water phase to each part of the oil phase. The same holds true for the $W_{80}8P$ formulation. Similarly, the ratio of Tri (N-butyl) phosphate:TRITON X-100:soybean oil also may be varied.

Although Table 1 lists specific amounts of glycerol monooleate, polysorbate 60, GENEROL 122, cetylpyridinium chloride, and carrier oil for $W_{80}8P$, these are merely exemplary. An emulsion that has the properties of $W_{80}8P$ may be formulated that has different concentrations of each of these components or indeed different components that will fulfill the same function. For example, the emulsion may have between about 80 to about 100 g of glycerol monooleate in the initial oil phase. In other embodiments, the emulsion may have between about 15 to about 30 g polysorbate 60 in the initial oil phase. In yet another embodiment the composition may comprise between about 20 to about 30 g of a GENEROL sterol, in the initial oil phase.

Individual components of nanoemulsions (e.g. in an immunogenic composition of the present invention) can function both to inactivate a pathogen as well as to contribute to the non-toxicity of the emulsions. For example, the active component in BCTP, TRITON-X100, shows less ability to inactivate a virus at concentrations equivalent to 11% BCTP. Adding the oil phase to the detergent and solvent markedly reduces the toxicity of these agents in tissue culture at the same concentrations. While not being bound to any theory (an understanding of the mechanism is not necessary to practice the present invention, and the present invention is not limited to any particular mechanism), it is suggested that the nanoemulsion enhances the interaction of its components with the pathogens thereby facilitating the inactivation of the pathogen and reducing the toxicity of the individual components. Furthermore, when all the components of BCTP are combined in one composition but are not in a nanoemulsion structure, the mixture is not as effective at inactivating a pathogen as when the components are in a nanoemulsion structure.

Numerous additional embodiments presented in classes of formulations with like compositions are presented below. The following compositions recite various ratios and mixtures of active components. One skilled in the art will appreciate that the below recited formulation are exemplary and that additional formulations comprising similar percent ranges of the recited components are within the scope of the present invention.

In certain embodiments of the present invention, a nanoemulsion comprises from about 3 to 8 vol. % of TYLOX-APOL, about 8 vol. % of ethanol, about 1 vol. % of cetylpyridinium chloride (CPC), about 60 to 70 vol. % oil (e.g., soybean oil), about 15 to 25 vol. % of aqueous phase (e.g., $DiH_2O$ or PBS), and in some formulations less than about 1 vol. % of 1N NaOH. Some of these embodiments comprise PBS. It is contemplated that the addition of 1N NaOH and/or PBS in some of these embodiments, allows the user to advantageously control the pH of the formulations, such that pH ranges from about 7.0 to about 9.0, and more preferably from about 7.1 to 8.5 are achieved. For example, one embodiment of the present invention comprises about 3 vol. % of TYLOX-APOL, about 8 vol. % of ethanol, about 1 vol. % of CPC, about 64 vol. % of soybean oil, and about 24 vol. % of $DiH_2O$ (designated herein as Y3EC). Another similar embodiment comprises about 3.5 vol. % of TYLOXAPOL, about 8 vol. % of ethanol, and about 1 vol. % of CPC, about 64 vol. % of soybean oil, and about 23.5 vol. % of DiH$_2$O (designated herein as Y3.5EC). Yet another embodiment comprises about 3 vol. % of TYLOXAPOL, about 8 vol. % of ethanol, about 1 vol. % of CPC, about 0.067 vol. % of 1N NaOH, such that the pH of the formulation is about 7.1, about 64 vol. % of soybean oil, and about 23.93 vol. % of DiH$_2$O (designated herein as Y3EC pH 7.1). Still another embodiment comprises about 3 vol. % of TYLOXAPOL, about 8 vol. % of ethanol, about 1 vol. % of CPC, about 0.67 vol. % of 1N NaOH, such that the pH of the formulation is about 8.5, and about 64 vol. % of soybean oil, and about 23.33 vol. % of DiH$_2$O (designated herein as Y3EC pH 8.5). Another similar embodiment comprises about 4% TYLOXAPOL, about 8 vol. % ethanol, about 1% CPC, and about 64 vol. % of soybean oil, and about 23 vol. % of DiH$_2$O (designated herein as Y4EC). In still another embodiment the formulation comprises about 8% TYLOXAPOL, about 8% ethanol, about 1 vol. % of CPC, and about 64 vol. % of soybean oil, and about 19 vol. % of DiH$_2$O (designated herein as Y8EC). A further embodiment comprises about 8 vol. % of TYLOXAPOL, about 8 vol. % of ethanol, about 1 vol. % of CPC, about 64 vol. % of soybean oil, and about 19 vol. % of 1×PBS (designated herein as Y8EC PBS).

In some embodiments of the present invention, a nanoemulsion comprises about 8 vol. % of ethanol, and about 1 vol. % of CPC, and about 64 vol. % of oil (e.g., soybean oil), and about 27 vol. % of aqueous phase (e.g., DiH$_2$O or PBS) (designated herein as EC).

In some embodiments, a nanoemulsion comprises from about 8 vol. % of sodium dodecyl sulfate (SDS), about 8 vol. % of tributyl phosphate (TBP), and about 64 vol. % of oil (e.g., soybean oil), and about 20 vol. % of aqueous phase (e.g., DiH$_2$O or PBS) (designated herein as S8P).

In some embodiments, a nanoemulsion comprises from about 1 to 2 vol. % of TRITON X-100, from about 1 to 2 vol. % of TYLOXAPOL, from about 7 to 8 vol. % of ethanol, about 1 vol. % of cetylpyridinium chloride (CPC), about 64 to 57.6 vol. % of oil (e.g., soybean oil), and about 23 vol. % of aqueous phase (e.g., DiH$_2$O or PBS). Additionally, some of these formulations further comprise about 5 mM of L-alanine/Inosine, and about 10 mM ammonium chloride. Some of these formulations comprise PBS. It is contemplated that the addition of PBS in some of these embodiments, allows the user to advantageously control the pH of the formulations. For example, one embodiment of the present invention comprises about 2 vol. % of TRITON X-100, about 2 vol. % of TYLOXAPOL, about 8 vol. % of ethanol, about 1 vol. % CPC, about 64 vol. % of soybean oil, and about 23 vol. % of aqueous phase DiH$_2$O. In another embodiment the formulation comprises about 1.8 vol. % of TRITON X-100, about 1.8 vol. % of TYLOXAPOL, about 7.2 vol. % of ethanol, about 0.9 vol. % of CPC, about 5 mM L-alanine/Inosine, and about 10 mM ammonium chloride, about 57.6 vol. % of soybean oil, and the remainder of 1×PBS (designated herein as 90% X2Y2EC/GE).

In alternative embodiments, a nanoemulsion comprises from about 5 vol. % of TWEEN 80, from about 8 vol. % of ethanol, from about 1 vol. % of CPC, about 64 vol. % of oil (e.g., soybean oil), and about 22 vol. % of DiH$_2$O (designated herein as W$_{80}$5EC). In yet another alternative embodiment, a nanoemulsion comprises from about 5 vol. % of TWEEN 80, from about 8 vol. % of ethanol, about 64 vol. % of oil (e.g., soybean oil), and about 23 vol. % of DiH$_2$O (designated herein as W$_{80}$5E).

In some embodiments, the present invention provides a nanoemulsion comprising from about 5 vol. % of Poloxamer-407, from about 8 vol. % of ethanol, from about 1 vol. % of CPC, about 64 vol. % of oil (e.g., soybean oil), and about 22 vol. % of DiH$_2$O (designated herein as P$_{407}$5EC). Although an understanding of the mechanism is not necessary to practice the present invention, and the present invention is not limited to any particular mechanism, in some embodiments, a nanoemulsion comprising Poloxamer-407 does not elicit and/or augment immune responses (e.g., in the lung) in a subject. In some embodiments, various dilutions of a nanoemulsion provided herein (e.g., P$_{407}$5EC) can be utilized to treat (e.g., kill and/or inhibit growth of) bacteria. In some embodiments, undiluted nanoemulsion is utilized. In some embodiments, P$_{407}$5EC is diluted (e.g., in serial, two fold dilutions) to obtain a desired concentration of one of the constituents of the nanoemulsion (e.g., CPC).

In still other embodiments of the present invention, a nanoemulsion comprises from about 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC).

In still other embodiments of the present invention, a nanoemulsion comprises from about 2 to 8 vol. % of TRITON X-100, about 8 vol. % of ethanol, about 1 vol. % of CPC, about 60 to 70 vol. % of oil (e.g., soybean, or olive oil), and about 15 to 25 vol. % of aqueous phase (e.g., DiH$_2$O or PBS). For example, the present invention contemplates formulations comprising about 2 vol. % of TRITON X-100, about 8 vol. % of ethanol, about 64 vol. % of soybean oil, and about 26 vol. % of DiH$_2$O (designated herein as X2E). In other similar embodiments, a nanoemulsion comprises about 3 vol. % of TRITON X-100, about 8 vol. % of ethanol, about 64 vol. % of soybean oil, and about 25 vol. % of DiH$_2$O (designated herein as X3E). In still further embodiments, the formulations comprise about 4 vol. % Triton of X-100, about 8 vol. % of ethanol, about 64 vol. % of soybean oil, and about 24 vol. % of DiH$_2$O (designated herein as X4E). In yet other embodiments, a nanoemulsion comprises about 5 vol. % of TRITON X-100, about 8 vol. % of ethanol, about 64 vol. % of soybean oil, and about 23 vol. % of DiH$_2$O (designated herein as X5E). In some embodiments, a nanoemulsion comprises about 6 vol. % of TRITON X-100, about 8 vol. % of ethanol, about 64 vol. % of soybean oil, and about 22 vol. % of DiH$_2$O (designated herein as X6E). In still further embodiments of the present invention, a nanoemulsion comprises about 8 vol. % of TRITON X-100, about 8 vol. % of ethanol, about 64 vol. % of soybean oil, and about 20 vol. % of DiH$_2$O (designated herein as X8E). In still further embodiments, a nanoemulsion comprises about 8 vol. % of TRITON X-100, about 8 vol. % of ethanol, about 64 vol. % of olive oil, and about 20 vol. % of DiH$_2$O (designated herein as X8E 0). In yet another embodiment, a nanoemulsion comprises 8 vol. % of TRITON X-100, about 8 vol. % ethanol, about 1 vol. % CPC, about 64 vol. % of soybean oil, and about 19 vol. % of DiH$_2$O (designated herein as X8EC).

In alternative embodiments of the present invention, a nanoemulsion comprises from about 1 to 2 vol. % of TRITON X-100, from about 1 to 2 vol. % of TYLOXAPOL, from about 6 to 8 vol. % TBP, from about 0.5 to 1.0 vol. % of CPC, from about 60 to 70 vol. % of oil (e.g., soybean), and about 1 to 35 vol. % of aqueous phase (e.g., DiH$_2$O or PBS). Additionally, certain of these nanoemulsions may comprise from about 1 to 5 vol. % of trypticase soy broth, from about 0.5 to 1.5 vol. % of yeast extract, about 5 mM L-alanine/Inosine, about 10 mM ammonium chloride, and from about 20-40 vol. % of liquid baby formula. In some embodiments comprising liquid baby formula, the formula comprises a casein hydrolysate (e.g., Neutramigen, or Progestimil, and the like). In some of these embodiments, a nanoemulsion further comprises from about 0.1 to 1.0 vol. % of sodium thiosulfate, and from about 0.1 to 1.0 vol. % of sodium citrate. Other similar embodiments comprising these basic components employ phosphate buffered saline (PBS) as the aqueous phase. For example, one embodiment comprises about 2 vol. % of TRITON X-100, about 2 vol. % TYLOXAPOL, about 8 vol. % TBP, about 1 vol. % of CPC, about 64 vol. % of soybean oil, and about 23 vol. % of DiH$_2$O (designated herein as X2Y2EC). In still other embodiments, the inventive formulation comprises about 2 vol. % of TRITON X-100, about 2 vol. % TYLOXAPOL, about 8 vol. % TBP, about 1 vol. % of CPC, about 0.9 vol. % of sodium thiosulfate, about 0.1 vol. % of sodium citrate, about 64 vol. % of soybean oil, and about 22 vol. % of DiH$_2$O (designated herein as X2Y2PC STS1). In another similar embodiment, a nanoemulsion comprises about 1.7 vol. % TRITON X-100, about 1.7 vol. % TYLOXAPOL, about 6.8 vol. % TBP, about 0.85% CPC, about 29.2% NEUTRAMIGEN, about 54.4 vol. % of soybean oil, and about 4.9 vol. % of DiH$_2$O (designated herein as 85% X2Y2PC/baby). In yet another embodiment of the present invention, a nanoemulsion comprises about 1.8 vol. % of TRITON X-100, about 1.8 vol. % of TYLOXAPOL, about 7.2 vol. % of TBP, about 0.9 vol. % of CPC, about 5 mM L-alanine/Inosine, about 10 mM ammonium chloride, about 57.6 vol. % of soybean oil, and the remainder vol. % of 0.1×PBS (designated herein as 90% X2Y2 PC/GE). In still another embodiment, a nanoemulsion comprises about 1.8 vol. % of TRITON X-100, about 1.8 vol. % of TYLOXAPOL, about 7.2 vol. % TBP, about 0.9 vol. % of CPC, and about 3 vol. % trypticase soy broth, about 57.6 vol. % of soybean oil, and about 27.7 vol. % of DiH$_2$O (designated herein as 90% X2Y2PC/TSB). In another embodiment of the present invention, a nanoemulsion comprises about 1.8 vol. % TRITON X-100, about 1.8 vol. % TYLOXAPOL, about 7.2 vol. % TBP, about 0.9 vol. % CPC, about 1 vol. % yeast extract, about 57.6 vol. % of soybean oil, and about 29.7 vol. % of DiH$_2$O (designated herein as 90% X2Y2PC/YE).

In some embodiments of the present invention, a nanoemulsion comprises about 3 vol. % of TYLOXAPOL, about 8 vol. % of TBP, and about 1 vol. % of CPC, about 60 to 70 vol. % of oil (e.g., soybean or olive oil), and about 15 to 30 vol. % of aqueous phase (e.g., DiH$_2$O or PBS). In a particular embodiment of the present invention, a nanoemulsion comprises about 3 vol. % of TYLOXAPOL, about 8 vol. % of TBP, and about 1 vol. % of CPC, about 64 vol. % of soybean, and about 24 vol. % of DiH$_2$O (designated herein as Y3PC).

In some embodiments of the present invention, a nanoemulsion comprises from about 4 to 8 vol. % of TRITON X-100, from about 5 to 8 vol. % of TBP, about 30 to 70 vol. % of oil (e.g., soybean or olive oil), and about 0 to 30 vol. % of aqueous phase (e.g., DiH$_2$O or PBS). Additionally, certain of these embodiments further comprise about 1 vol. % of CPC, about 1 vol. % of benzalkonium chloride, about 1 vol. % cetylpyridinium bromide, about 1 vol. % cetyldimethyletylammonium bromide, 500 µM EDTA, about 10 mM ammonium chloride, about 5 mM Inosine, and about 5 mM L-alanine. For example, in a certain preferred embodiment, a nanoemulsion comprises about 8 vol. % of TRITON X-100, about 8 vol. % of TBP, about 64 vol. % of soybean oil, and about 20 vol. % of DiH$_2$O (designated herein as X8P). In another embodiment of the present invention, a nanoemulsion comprises about 8 vol. % of TRITON X-100, about 8 vol. % of TBP, about 1% of CPC, about 64 vol. % of soybean oil, and about 19 vol. % of DiH$_2$O (designated herein as X8PC). In still another embodiment, a nanoemulsion comprises about 8 vol. % TRITON X-100, about 8 vol. % of TBP, about 1 vol. % of CPC, about 50 vol. % of soybean oil, and about 33 vol. % of DiH$_2$O (designated herein as ATB-X1001). In yet another embodiment, the formulations comprise about 8 vol. % of TRITON X-100, about 8 vol. % of TBP, about 2 vol. % of CPC, about 50 vol. % of soybean oil, and about 32 vol. % of DiH$_2$O (designated herein as ATB-X002). In some embodiments, a nanoemulsion comprises about 4 vol. % TRITON X-100, about 4 vol. % of TBP, about 0.5 vol. % of CPC, about 32 vol. % of soybean oil, and about 59.5 vol. % of DiH$_2$O (designated herein as 50% X8PC). In some embodiments, a nanoemulsion comprises about 8 vol. % of TRITON X-100, about 8 vol. % of TBP, about 0.5 vol. % CPC, about 64 vol. % of soybean oil, and about 19.5 vol. % of DiH$_2$O (designated herein as X8PC$_{1/2}$). In some embodiments of the present invention, a nanoemulsion comprises about 8 vol. % of TRITON X-100, about 8 vol. % of TBP, about 2 vol. % of CPC, about 64 vol. % of soybean oil, and about 18 vol. % of DiH$_2$O (designated herein as X8PC2). In other embodiments, a nanoemulsion comprises about 8 vol. % of TRITON X-100, about 8% of TBP, about 1% of benzalkonium chloride, about 50 vol. % of soybean oil, and about 33 vol. % of DiH$_2$O (designated herein as X8P BC). In an alternative embodiment of the present invention, a nanoemulsion comprises about 8 vol. % of TRITON X-100, about 8 vol. % of TBP, about 1 vol. % of cetylyridinium bromide, about 50 vol. % of soybean oil, and about 33 vol. % of DiH$_2$O (designated herein as X8P CPB). In another exemplary embodiment of the present invention, a nanoemulsion comprises about 8 vol. % of TRITON X-100, about 8 vol. % of TBP, about 1 vol. % of cetyldimethyletylammonium bromide, about 50 vol. % of soybean oil, and about 33 vol. % of DiH$_2$O (designated herein as X8P CTAB). In still further embodiments, a nanoemulsion comprises about 8 vol. % of TRITON X-100, about 8 vol. % of TBP, about 1 vol. % of CPC, about 500 µM EDTA, about 64 vol. % of soybean oil, and about 15.8 vol. % DiH$_2$O (designated herein as X8PC EDTA). In some embodiments, a nanoemulsion comprises 8 vol. % of TRITON X-100, about 8 vol. % of TBP, about 1 vol. % of CPC, about 10 mM ammonium chloride, about 5 mM Inosine, about 5 mM L-alanine, about 64 vol. % of soybean oil, and about 19 vol. % of DiH$_2$O or PBS (designated herein as X8PC GE$_{1x}$). In another embodiment of the present invention, a nanoemulsion comprises about 5 vol. % of TRITON X-100, about 5% of TBP, about 1 vol. % of CPC, about 40 vol. % of soybean oil, and about 49 vol. % of DiH$_2$O (designated herein as X5P$_5$C).

In some embodiments of the present invention, a nanoemulsion comprises about 2 vol. % TRITON X-100, about 6 vol. % TYLOXAPOL, about 8 vol. % ethanol, about 64 vol. % of soybean oil, and about 20 vol. % of DiH$_2$O (designated herein as X2Y6E).

In an additional embodiment of the present invention, a nanoemulsion comprises about 8 vol. % of TRITON X-100, and about 8 vol. % of glycerol, about 60 to 70 vol. % of oil (e.g., soybean or olive oil), and about 15 to 25 vol. % of aqueous phase (e.g., DiH$_2$O or PBS). Certain nanoemulsion compositions (e.g., used to generate an immune response (e.g., for use as a vaccine) comprise about 1 vol. % L-ascorbic acid. For example, one particular embodiment comprises about 8 vol. % of TRITON X-100, about 8 vol. % of glycerol, about 64 vol. % of soybean oil, and about 20 vol. % of DiH$_2$O (designated herein as X8G). In still another embodiment, a nanoemulsion comprises about 8 vol. % of TRITON X-100, about 8 vol. % of glycerol, about 1 vol. % of L-ascorbic acid, about 64 vol. % of soybean oil, and about 19 vol. % of DiH$_2$O (designated herein as X8GV$_c$).

In still further embodiments, a nanoemulsion comprises about 8 vol. % of TRITON X-100, from about 0.5 to 0.8 vol. % of TWEEN 60, from about 0.5 to 2.0 vol. % of CPC, about 8 vol. % of TBP, about 60 to 70 vol. % of oil (e.g., soybean or olive oil), and about 15 to 25 vol. % of aqueous phase (e.g., DiH$_2$O or PBS). For example, in one particular embodiment a nanoemulsion comprises about 8 vol. % of TRITON X-100, about 0.70 vol. % of TWEEN 60, about 1 vol. % of CPC, about 8 vol. % of TBP, about 64 vol. % of soybean oil, and about 18.3 vol. % of DiH$_2$O (designated herein as X8W60PC$_1$). In some embodiments, a nanoemulsion comprises about 8 vol. % of TRITON X-100, about 0.71 vol. % of TWEEN 60, about 1 vol. % of CPC, about 8 vol. % of TBP, about 64 vol. % of soybean oil, and about 18.29 vol. % of DiH$_2$O (designated herein as W60$_{0.7}$X8PC). In yet other embodiments, a nanoemulsion comprises from about 8 vol. % of TRITON X-100, about 0.7 vol. % of TWEEN 60, about 0.5 vol. % of CPC, about 8 vol. % of TBP, about 64 to 70 vol. % of soybean oil, and about 18.8 vol. % of DiH$_2$O (designated herein as X8W60PC$_2$). In still other embodiments, a nanoemulsion comprises about 8 vol. % of TRITON X-100, about 0.71 vol. % of TWEEN 60, about 2 vol. % of CPC, about 8 vol. % of TBP, about 64 vol. % of soybean oil, and about 17.3 vol. % of DiH$_2$O. In another embodiment of the present invention, a nanoemulsion comprises about 0.71 vol. % of TWEEN 60, about 1 vol. % of CPC, about 8 vol. % of TBP, about 64 vol. % of soybean oil, and about 25.29 vol. % of DiH$_2$O (designated herein as W60$_{0.7}$PC).

In another embodiment of the present invention, a nanoemulsion comprises about 2 vol. % of dioctyl sulfosuccinate, either about 8 vol. % of glycerol, or about 8 vol. % TBP, in addition to, about 60 to 70 vol. % of oil (e.g., soybean or olive oil), and about 20 to 30 vol. % of aqueous phase (e.g., DiH$_2$O or PBS). For example, in some embodiments, a nanoemulsion comprises about 2 vol. % of dioctyl sulfosuccinate, about 8 vol. % of glycerol, about 64 vol. % of soybean oil, and about 26 vol. % of DiH$_2$O (designated as D2G). In another related embodiment, a nanoemulsion comprises about 2 vol. % of dioctyl sulfosuccinate, and about 8 vol. % of TBP, about 64 vol. % of soybean oil, and about 26 vol. % of DiH$_2$O (designated herein as D2P).

In still other embodiments of the present invention, a nanoemulsion comprises about 8 to 10 vol. % of glycerol, and about 1 to 10 vol. % of CPC, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprises about 1 vol. % of L-ascorbic acid. For example, in some embodiments, a nanoemulsion comprises about 8 vol. % of glycerol, about 1 vol. % of CPC, about 64 vol. % of soybean oil, and about 27 vol. % of DiH$_2$O (designated herein as GC). In some embodiments, a nanoemulsion comprises about 10 vol. % of glycerol, about 10 vol. % of CPC, about 60 vol. % of soybean oil, and about 20 vol. % of DiH$_2$O (designated herein as GC10). In still another embodiment of the present invention, a nanoemulsion comprises about 10 vol. % of glycerol, about 1 vol. % of CPC, about 1 vol. % of L-ascorbic acid, about 64 vol. % of soybean or oil, and about 24 vol. % of DiH$_2$O (designated herein as GCV$_c$).

In some embodiments of the present invention, a nanoemulsion comprises about 8 to 10 vol. % of glycerol, about 8 to 10 vol. % of SDS, about 50 to 70 vol. % of oil (e.g., soybean or olive oil), and about 15 to 30 vol. % of aqueous phase (e.g., DiH$_2$O or PBS). Additionally, in certain of these embodiments, a nanoemulsion further comprise about 1 vol. % of lecithin, and about 1 vol. % of p-Hydroxybenzoic acid methyl ester. Exemplary embodiments of such formulations comprise about 8 vol. % SDS, 8 vol. % of glycerol, about 64 vol. % of soybean oil, and about 20 vol. % of DiH$_2$O (designated herein as S8G). A related formulation comprises about 8 vol. % of glycerol, about 8 vol. % of SDS, about 1 vol. % of lecithin, about 1 vol. % of p-Hydroxybenzoic acid methyl ester, about 64 vol. % of soybean oil, and about 18 vol. % of DiH$_2$O (designated herein as S8GL1B1).

In yet another embodiment of the present invention, a nanoemulsion comprises about 4 vol. % of TWEEN 80, about 4 vol. % of TYLOXAPOL, about 1 vol. % of CPC, about 8 vol. % of ethanol, about 64 vol. % of soybean oil, and about 19 vol. % of DiH$_2$O (designated herein as W$_{80}$4Y4EC).

In some embodiments of the present invention, a nanoemulsion comprises about 0.01 vol. % of CPC, about 0.08 vol. % of TYLOXAPOL, about 10 vol. % of ethanol, about 70 vol. % of soybean oil, and about 19.91 vol. % of DiH$_2$O (designated herein as Y.08EC.01).

In yet another embodiment of the present invention, a nanoemulsion comprises about 8 vol. % of sodium lauryl sulfate, and about 8 vol. % of glycerol, about 64 vol. % of soybean oil, and about 20 vol. % of DiH$_2$O (designated herein as SLS8G).

The specific formulations described above are simply examples to illustrate the variety of nanoemulsion adjuvants that find use in the present invention. The present invention contemplates that many variations of the above formulations, as well as additional nanoemulsions, find use in the methods of the present invention. Candidate emulsions can be easily tested to determine if they are suitable. First, the desired ingredients are prepared using the methods described herein, to determine if an emulsion can be formed. If an emulsion cannot be formed, the candidate is rejected. For example, a candidate composition made of 4.5% sodium thiosulfate, 0.5% sodium citrate, 10% n-butanol, 64% soybean oil, and 21% DiH$_2$O does not form an emulsion.

Second, the candidate emulsion should form a stable emulsion. An emulsion is stable if it remains in emulsion form for a sufficient period to allow its intended use (e.g., to generate an immune response in a subject). For example, for emulsions that are to be stored, shipped, etc., it may be desired that the composition remain in emulsion form for months to years. Typical emulsions that are relatively unstable, will lose their form within a day. For example, a candidate composition made of 8% 1-butanol, 5% TWEEN 10, 1% CPC, 64% soybean oil, and 22% DiH$_2$O does not form a stable emulsion. Nanoemulsions that have been shown to be stable include, but are not limited to, 8 vol. % of TRITON X-100, about 8 vol. % of TBP, about 64 vol. % of soybean oil, and about 20 vol. % of DiH$_2$O (designated herein as X8P); 5 vol. % of TWEEN 20, from about 8 vol. % of ethanol, from about 1 vol. % of CPC, about 64 vol. % of oil (e.g., soybean oil), and about 22 vol. % of DiH$_2$O (designated herein as W$_{20}$5EC); 0.08% Triton X-100, 0.08% Glycerol, 0.01% Cetylpyridinium Chloride, 99% Butter, and 0.83% diH$_2$O (designated herein as 1% X8GC Butter); 0.8% Triton X-100, 0.8% Glycerol, 0.1% Cetylpyridinium Chloride, 6.4% Soybean Oil, 1.9% diH$_2$O, and 90% Butter (designated herein as 10% X8GC Butter); 2% W$_{20}$5EC, 1% Natrosol 250L NF, and 97% diH$_2$O (designated herein as 2% W$_{20}$5EC L GEL); 1% Cetylpyridinium Chloride, 5% TWEEN 20, 8% Ethanol, 64% 70 Viscosity Mineral Oil, and 22% diH$_2$O (designated herein as W$_{20}$5EC70 Mineral Oil); 1% Cetylpyridinium Chloride, 5% TWEEN 20, 8% Ethanol, 64% 350 Viscosity Mineral Oil, and 22% diH$_2$O (designated herein as W$_{20}$5EC350 Mineral Oil). In some embodiments, nanoemulsions of the present invention are stable for over a week, over a month, or over a year.

Third, the candidate emulsion should have efficacy for its intended use. For example, a nanoemulsion should inactivate (e.g., kill or inhibit growth of) a pathogen to a desired level (e.g., 1 log, 2 log, 3 log, 4 log, . . . reduction). Using the methods described herein, one is capable of determining the suitability of a particular candidate emulsion against the desired pathogen. Generally, this involves exposing the pathogen to the emulsion for one or more time periods in a side-by-side experiment with the appropriate control samples (e.g., a negative control such as water) and determining if, and to what degree, the emulsion inactivates (e.g., kills and/or neutralizes) the microorganism. For example, a candidate composition made of 1% ammonium chloride, 5% TWEEN 20, 8% ethanol, 64% soybean oil, and 22% DiH$_2$O was shown not to be an effective emulsion. The following candidate emulsions were shown to be effective using the methods described herein: 5% TWEEN 20, 5% Cetylpyridinium Chloride, 10% Glycerol, 60% Soybean Oil, and 20% diH$_2$O (designated herein as $W_{20}5GC5$); 1% Cetylpyridinium Chloride, 5% TWEEN 20, 10% Glycerol, 64% Soybean Oil, and 20% diH$_2$O (designated herein as $W_{20}5GC$); 1% Cetylpyridinium Chloride, 5% TWEEN 20, 8% Ethanol, 64% Olive Oil, and 22% diH$_2$O (designated herein as $W_{20}5EC$ Olive Oil); 1% Cetylpyridinium Chloride, 5% TWEEN 20, 8% Ethanol, 64% Flaxseed Oil, and 22% diH$_2$O (designated herein as $W_{20}5EC$ Flaxseed Oil); 1% Cetylpyridinium Chloride, 5% TWEEN 20, 8% Ethanol, 64% Corn Oil, and 22% diH$_2$O (designated herein as $W_{20}5EC$ Corn Oil); 1% Cetylpyridinium Chloride, 5% TWEEN 20, 8% Ethanol, 64% Coconut Oil, and 22% diH$_2$O (designated herein as $W_{20}5EC$ Coconut Oil); 1% Cetylpyridinium Chloride, 5% TWEEN 20, 8% Ethanol, 64% Cottonseed Oil, and 22% diH$_2$O (designated herein as $W_{20}5EC$ Cottonseed Oil); 8% Dextrose, 5% TWEEN 10, 1% Cetylpyridinium Chloride, 64% Soybean Oil, and 22% diH$_2$O (designated herein as $W_{20}5C$ Dextrose); 8% PEG 200, 5% TWEEN 10, 1% Cetylpyridinium Chloride, 64% Soybean Oil, and 22% diH$_2$O (designated herein as $W_{20}5C$ PEG 200); 8% Methanol, 5% TWEEN 10, 1% Cetylpyridinium Chloride, 64% Soybean Oil, and 22% diH$_2$O (designated herein as $W_{20}5C$ Methanol); 8% PEG 1000, 5% TWEEN 10, 1% Cetylpyridinium Chloride, 64% Soybean Oil, and 22% diH$_2$O (designated herein as $W_{20}5C$ PEG 1000); 2% $W_{20}5EC$, 2% Natrosol 250H NF, and 96% diH$_2$O (designated herein as 2% $W_{20}5EC$ Natrosol 2, also called 2% $W_{20}5EC$ GEL); 2% $W_{20}5EC$, 1% Natrosol 250H NF, and 97% diH$_2$O (designated herein as 2% $W_{20}5EC$ Natrosol 1); 2% $W_{20}5EC$, 3% Natrosol 250H NF, and 95% diH$_2$O (designated herein as 2% $W_{20}5EC$ Natrosol 3); 2% $W_{20}5EC$, 0.5% Natrosol 250H NF, and 97.5% diH$_2$O (designated herein as 2% $W_{20}5EC$ Natrosol 0.5); 2% $W_{20}5EC$, 2% Methocel A, and 96% diH$_2$O (designated herein as 2% $W_{20}5EC$ Methocel A); 2% $W_{20}5EC$, 2% Methocel K, and 96% diH$_2$O (designated herein as 2% $W_{20}5EC$ Methocel K); 2% Natrosol, 0.1% X8PC, 0.1×PBS, 5 mM L-alanine, 5 mM Inosine, 10 mM Ammonium Chloride, and diH$_2$O (designated herein as 0.1% X8PC/GE+2% Natrosol); 2% Natrosol, 0.8% Triton X-100, 0.8% Tributyl Phosphate, 6.4% Soybean Oil, 0.1% Cetylpyridinium Chloride, 0.1×PBS, 5 mM L-alanine, 5 mM Inosine, 10 mM Ammonium Chloride, and diH$_2$O (designated herein as 10% X8PC/GE+2% Natrosol); 1% Cetylpyridinium Chloride, 5% TWEEN 20, 8% Ethanol, 64% Lard, and 22% diH$_2$O (designated herein as $W_{20}5EC$ Lard); 1% Cetylpyridinium Chloride, 5% TWEEN 20, 8% Ethanol, 64% Mineral Oil, and 22% diH$_2$O (designated herein as $W_{20}5EC$ Mineral Oil); 0.1% Cetylpyridinium Chloride, 2% Nerolidol, 5% TWEEN 20, 10% Ethanol, 64% Soybean Oil, and 18.9% diH$_2$O (designated herein as $W_{20}5EC_{0.1}N$); 0.1% Cetylpyridinium Chloride, 2% Farnesol, 5% TWEEN 20, 10% Ethanol, 64% Soybean Oil, and 18.9% diH$_2$O (designated herein as $W_{20}5EC_{0.1}F$); 0.1% Cetylpyridinium Chloride, 5% TWEEN 20, 10% Ethanol, 64% Soybean Oil, and 20.9% diH$_2$O (designated herein as $W_{20}5EC_{0.1}$); 10% Cetylpyridinium Chloride, 8% Tributyl Phosphate, 8% Triton X-100, 54% Soybean Oil, and 20% diH$_2$O (designated herein as $X8PC_{10}$); 5% Cetylpyridinium Chloride, 8% Triton X-100, 8% Tributyl Phosphate, 59% Soybean Oil, and 20% diH$_2$O (designated herein as $X8PC_5$); 0.02% Cetylpyridinium Chloride, 0.1% TWEEN 20, 10% Ethanol, 70% Soybean Oil, and 19.88% diH$_2$O (designated herein as $W_{20}0.1EC_{0.02}$); 1% Cetylpyridinium Chloride, 5% TWEEN 20, 8% Glycerol, 64% Mobil 1, and 22% diH$_2$O (designated herein as $W_{20}5GC$ Mobil 1); 7.2% Triton X-100, 7.2% Tributyl Phosphate, 0.9% Cetylpyridinium Chloride, 57.6% Soybean Oil, 0.1×PBS, 5 mM L-alanine, 5 mM Inosine, 10 mM Ammonium Chloride, and 25.87% diH$_2$O (designated herein as 90% X8PC/GE); 7.2% Triton X-100, 7.2% Tributyl Phosphate, 0.9% Cetylpyridinium Chloride, 57.6% Soybean Oil, 1% EDTA, 5 mM L-alanine, 5 mM Inosine, 10 mM Ammonium Chloride, 0.1× PBS, and diH$_2$O (designated herein as 90% X8PC/GE EDTA); and 7.2% Triton X-100, 7.2% Tributyl Phosphate, 0.9% Cetylpyridinium Chloride, 57.6% Soybean Oil, 1% Sodium Thiosulfate, 5 mM L-alanine, 5 mM Inosine, 10 mM Ammonium Chloride, 0.1×PBS, and diH$_2$O (designated herein as 90% X8PC/GE STS).

In preferred embodiments of the present invention, the nanoemulsions are non-toxic (e.g., to humans, plants, or animals), non-irritant (e.g., to humans, plants, or animals), and non-corrosive (e.g., to humans, plants, or animals or the environment), while retaining stability when mixed with other agents (e.g., a composition comprising an immunogen (e.g., bacteria, fungi, viruses, and spores). While a number of the above described nanoemulsions meet these qualifications, the following description provides a number of preferred non-toxic, non-irritant, non-corrosive, anti-microbial nanoemulsions of the present invention (hereinafter in this section referred to as "non-toxic nanoemulsions").

In some embodiments the non-toxic nanoemulsions comprise surfactant lipid preparations (SLPs) for use as broad-spectrum antimicrobial agents that are effective against bacteria and their spores, enveloped viruses, and fungi. In preferred embodiments, these SLPs comprise a mixture of oils, detergents, solvents, and cationic halogen-containing compounds in addition to several ions that enhance their biocidal activities. These SLPs are characterized as stable, non-irritant, and non-toxic compounds compared to commercially available bactericidal and sporicidal agents, which are highly irritant and/or toxic.

Ingredients for use in the non-toxic nanoemulsions include, but are not limited to: detergents (e.g., TRITON X-100 (5-15%) or other members of the TRITON family, TWEEN 60 (0.5-2%) or other members of the TWEEN family, or TYLOXAPOL (1-10%)); solvents (e.g., tributyl phosphate (5-15%)); alcohols (e.g., ethanol (5-15%) or glycerol (5-15%)); oils (e.g., soybean oil (40-70%)); cationic halogen-containing compounds (e.g., cetylpyridinium chloride (0.5-2%), cetylpyridinium bromide (0.5-2%)), or cetyldimethylethyl ammonium bromide (0.5-2%)); quaternary ammonium compounds (e.g., benzalkonium chloride (0.5-2%), N-alkyldimethylbenzyl ammonium chloride (0.5-2%)); ions (calcium chloride (1 mM-40 mM), ammonium chloride (1 mM-20 mM), sodium chloride (5 mM-200 mM), sodium phosphate (1 mM-20 mM)); nucleosides (e.g., inosine (50

µM-20 mM)); and amino acids (e.g., L-alanine (50 µM-20 mM)). Emulsions are prepared, for example, by mixing in a high shear mixer for 3-10 minutes. The emulsions may or may not be heated before mixing at 82° C. for 1 hour.

Quaternary ammonium compounds for use in the present include, but are not limited to, N-alkyldimethyl benzyl ammonium saccharinate; 1,3,5-Triazine-1,3,5(2H, 4H, 6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxyethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl(ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethyylbenzyl ammonium chloride; and n-octadecyl dimethyl benzyl ammonium chloride.

1. Aqueous Phase

In some embodiments, the emulsion comprises an aqueous phase. In certain preferred embodiments, the emulsion comprises about 5 to 50, preferably 10 to 40, more preferably 15 to 30, vol. % aqueous phase, based on the total volume of the emulsion (although other concentrations are also contemplated). In preferred embodiments, the aqueous phase comprises water at a pH of about 4 to 10, preferably about 6 to 8. The water is preferably deionized (hereinafter "DiH$_2$O"). In some embodiments, the aqueous phase comprises phosphate buffered saline (PBS). In some preferred embodiments, the aqueous phase is sterile and pyrogen free.

2. Oil Phase

In some embodiments, the emulsion comprises an oil phase. In certain preferred embodiments, the oil phase (e.g., carrier oil) of the emulsion of the present invention comprises 30-90, preferably 60-80, and more preferably 60-70, vol. % of oil, based on the total volume of the emulsion (although higher and lower concentrations also find use in emulsions described herein).

The oil in the nanoemulsion adjuvant of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, *chenopodium* oil, citronellal, citral, citronellol, chamazulene, yarrow, guaiazulene, chamomile, semi-synthetic derivatives, or combinations thereof.

In one aspect of the invention, the volatile oil in the silicone component is different than the oil in the oil phase.

In some embodiments, the oil phase comprises 3-15, and preferably 5-10 vol. % of an organic solvent, based on the total volume of the emulsion. While the present invention is not limited to any particular mechanism, it is contemplated that the organic phosphate-based solvents employed in the emulsions serve to remove or disrupt the lipids in the membranes of the pathogens. Thus, any solvent that removes the sterols or phospholipids in the microbial membranes finds use in the methods of the present invention. Suitable organic solvents include, but are not limited to, organic phosphate based solvents or alcohols. In some preferred embodiments, non-toxic alcohols (e.g., ethanol) are used as a solvent. The oil phase, and any additional compounds provided in the oil phase, are preferably sterile and pyrogen free.

3. Surfactants and Detergents

In some embodiments, the emulsions further comprises a surfactant or detergent. In some preferred embodiments, the emulsion comprises from about 3 to 15%, and preferably about 10% of one or more surfactants or detergents (although other concentrations are also contemplated). While the present invention is not limited to any particular mechanism, it is contemplated that surfactants, when present in the emulsions, help to stabilize the emulsions. Both non-ionic (non-anionic) and ionic surfactants are contemplated. Additionally, surfactants from the BRIJ family of surfactants find use in the compositions of the present invention. The surfactant can be provided in either the aqueous or the oil phase. Surfactants suitable for use with the emulsions include a variety of anionic and nonionic surfactants, as well as other emulsifying compounds that are capable of promoting the formation of oil-in-water emulsions. In general, emulsifying compounds are relatively hydrophilic, and blends of emulsifying compounds can be used to achieve the necessary qualities. In some formulations, nonionic surfactants have advantages over ionic emulsifiers in that they are substantially more compatible with a broad pH range and often form more stable emulsions than do ionic (e.g., soap-type) emulsifiers.

The surfactant in the nanoemulsion adjuvant of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference. Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thighlycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isoproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23. In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from *Quillaja* bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-Triazine-1,3,5(2H, 4H, 6H)-triethanol, 1-Decanaminium, N-decyl-N,N-dimethyl-, chloride, Didecyl dimethyl ammonium chloride, 2-(2-(p-(Diisobutyl) cresosxy)ethoxy)ethyl dimethyl benzyl ammonium chloride, 2-(2-(p-(Diisobutyl)phenoxy)ethoxy)ethyl dimethyl benzyl ammonium chloride, Alkyl 1 or 3 benzyl-1-(2-hydroxethyl)-2-imidazolinium chloride, Alkyl bis(2-hydroxyethyl)benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl dimethyl benzyl ammonium chloride, Alkyl didecyl dimethyl ammonium chloride, Alkyl dimethyl benzyl ammonium chloride, Alkyl dimethyl ammonium chloride (C12-16), Alkyl dimethyl benzyl ammonium chloride (C12-18), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 30% C14, 17% C16, 3% C18), Alkyl trimethyl ammonium chloride (58% C18, 40% C16, 1% C14, 1% C12), Alkyl trimethyl ammonium chloride (90% C18, 10% C16), Alkyldimethyl (ethylbenzyl) ammonium chloride (C12-18), Di-(C8-10)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis(2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio)propanesulfonate inner salt, 3-(N,N-Dimethylpalmitylammonio)propanesulfonate, semi-synthetic derivatives thereof, and combinations thereof.

The present invention is not limited to the surfactants disclosed herein. Additional surfactants and detergents useful in the compositions of the present invention may be ascertained from reference works (e.g., including, but not limited to, McCutheon's Volume 1: Emulsions and Detergents—North American Edition, 2000) and commercial sources.

4. Cationic Halogens Containing Compounds

In some embodiments, the emulsions further comprise a cationic halogen containing compound. In some preferred embodiments, the emulsion comprises from about 0.5 to 1.0 wt. % or more of a cationic halogen containing compound, based on the total weight of the emulsion (although other concentrations are also contemplated). In preferred embodiments, the cationic halogen-containing compound is preferably premixed with the oil phase; however, it should be understood that the cationic halogen-containing compound may be provided in combination with the emulsion composition in a distinct formulation. Suitable halogen containing compounds may be selected from compounds comprising chloride, fluoride, bromide and iodide ions. In preferred embodiments, suitable cationic halogen containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), and cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen-containing compound is CPC, although the compositions of the present invention are not limited to formulation with any particular cationic containing compound.

5. Germination Enhancers

In other embodiments of the present invention, the nanoemulsions further comprise a germination enhancer. In some preferred embodiments, the emulsions comprise from about 1 mM to 15 mM, and more preferably from about 5 mM to 10 mM of one or more germination enhancing compounds (although other concentrations are also contemplated). In preferred embodiments, the germination enhancing compound is provided in the aqueous phase prior to formation of the emulsion. The present invention contemplates that when germination enhancers are added to the nanoemulsion compositions, the sporicidal properties of the nanoemulsions are enhanced. The present invention further contemplates that such germination enhancers initiate sporicidal activity near neutral pH (between pH 6-8, and preferably 7). Such neutral pH emulsions can be obtained, for example, by diluting with phosphate buffer saline (PBS) or by preparations of neutral emulsions. The sporicidal activity of the nanoemulsion preferentially occurs when the spores initiate germination.

In specific embodiments, it has been demonstrated that the emulsions utilized in the vaccines of the present invention have sporicidal activity. While the present invention is not limited to any particular mechanism and an understanding of the mechanism is not required to practice the present invention, it is believed that the fusigenic component of the emulsions acts to initiate germination and before reversion to the vegetative form is complete the lysogenic component of the emulsion acts to lyse the newly germinating spore. These components of the emulsion thus act in concert to leave the spore susceptible to disruption by the emulsions. The addition of germination enhancer further facilitates the anti-sporicidal activity of the emulsions, for example, by speeding up the rate at which the sporicidal activity occurs.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine stimulates bacterial spore germination (See e.g., Hills, J. Gen. Micro. 4:38 (1950); and Halvorson and Church, Bacteriol Rev. 21:112 (1957)). L-alanine and L-proline have also been reported to initiate fungal spore germination (Yanagita, Arch Mikrobiol 26:329 (1957)). Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate, which is the end product of glycolytic metabolism (EmBECTON DICKENSONen-Meyerhof-Parnas Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle), which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

In certain embodiments, suitable germination enhancing agents of the invention include, but are not limited to, -amino acids comprising glycine and the L-enantiomers of alanine, valine, leucine, isoleucine, serine, threonine, lysine, phenylalanine, tyrosine, and the alkyl esters thereof. Additional information on the effects of amino acids on germination may be found in U.S. Pat. No. 5,510,104; herein incorporated by reference in its entirety. In some embodiments, a mixture of glucose, fructose, asparagine, sodium chloride (NaCl), ammonium chloride ($NH_4Cl$), calcium chloride ($CaCl_2$) and potassium chloride (KCl) also may be used. In particularly preferred embodiments of the present invention, the formulation comprises the germination enhancers L-alanine, $CaCl_2$, Inosine and $NH_4Cl$. In some embodiments, the compositions further comprise one or more common forms of growth media (e.g., trypticase soy broth, and the like) that additionally may or may not itself comprise germination enhancers and buffers.

The above compounds are merely exemplary germination enhancers and it is understood that other known germination enhancers will find use in the nanoemulsions utilized in some embodiments of the present invention. A candidate germination enhancer should meet two criteria for inclusion in the compositions of the present invention: it should be capable of being associated with the emulsions disclosed herein and it should increase the rate of germination of a target spore when incorporated in the emulsions disclosed herein. One skilled in the art can determine whether a particular agent has the desired function of acting as an germination enhancer by applying such an agent in combination with the nanoemulsions disclosed herein to a target and comparing the inactivation of the target when contacted by the admixture with inactivation of like targets by the composition of the present invention without the agent. Any agent that increases germination, and thereby decreases or inhibits the growth of the organisms, is considered a suitable enhancer for use in the nanoemulsion compositions disclosed herein.

In still other embodiments, addition of a germination enhancer (or growth medium) to a neutral emulsion composition produces a composition that is useful in inactivating bacterial spores in addition to enveloped viruses, Gram negative bacteria, and Gram positive bacteria for use in the vaccine compositions of the present invention.

6. Interaction Enhancers

In still other embodiments, nanoemulsions comprise one or more compounds capable of increasing the interaction of the compositions (i.e., "interaction enhancer" (e.g., with target pathogens (e.g., the cell wall of Gram negative bacteria such as *Vibrio, Salmonella, Shigella* and *Pseudomonas*)). In preferred embodiments, the interaction enhancer is preferably premixed with the oil phase; however, in other embodiments the interaction enhancer is provided in combination with the compositions after emulsification. In certain preferred embodiments, the interaction enhancer is a chelating agent (e.g., ethylenediaminetetraacetic acid (EDTA) or ethylenebis(oxyethylenenitrilo)tetraacetic acid (EGTA) in a buffer (e.g., tris buffer)). It is understood that chelating agents are merely exemplary interaction enhancing compounds. Indeed, other agents that increase the interaction of the nanoemulsions used in some embodiments of the present invention (e.g., with microbial agents, pathogens, vaccines, etc.) are contemplated. In particularly preferred embodiments, the interaction enhancer is at a concentration of about 50 to about 250 μM. One skilled in the art will be able to determine whether a particular agent has the desired function of acting as an interaction enhancer by applying such an agent in combination with the compositions of the present invention to a target and comparing the inactivation of the target when contacted by the admixture with inactivation of like targets by the composition of the present invention without the agent. Any agent that increases the interaction of an emulsion with bacteria and thereby decreases or inhibits the growth of the bacteria, in comparison to that parameter in its absence, is considered an interaction enhancer.

In some embodiments, the addition of an interaction enhancer to nanoemulsion produces a composition that is useful in inactivating enveloped viruses, some Gram positive bacteria and some Gram negative bacteria for use in a vaccine composition.

7. Quaternary Ammonium Compounds

In some embodiments, nanoemulsions of the present invention include a quaternary ammonium containing compound. Exemplary quaternary ammonium compounds include, but are not limited to, Alkyl dimethyl benzyl ammonium chloride, didecyl dimethyl ammonium chloride, Alkyl dimethyl benzyl and dialkyl dimethyl ammonium chloride, N,N-Dimethyl-2-hydroxypropylammonium chloride polymer, Didecyl dimethyl ammonium chloride, n-Alkyl dimethyl benzyl ammonium chloride, n-Alkyl dimethyl ethylbenzyl ammonium chloride, Dialkyl dimethyl ammonium chloride, n-Alkyl dimethyl benzyl ammonium chloride, n-Tetradecyl dimethyl benzyl ammonium chloride monohydrate, n-Alkyl dimethyl benzyl ammonium chloride, Dialkyl dimethyl ammonium chloride, Hexahydro-1,3,5-tris(2-hydroxyethyl)-s-triazine, Myristalkonium chloride (and) Quat RNIUM 14, Alkyl bis(2-hydroxyethyl)benzyl ammonium chloride, Alkyl demethyl benzyl ammonium chloride, Alkyl dimethyl 3,4-dichlorobenzyl ammonium chloride, Alkyl dimethyl benzyl ammonium chloride, Alkyl dimethyl benzyl dimethylbenzyl ammonium, Alkyl dimethyl dimethybenzyl ammonium chloride, Alkyl dimethyl ethyl ammonium bromide, Alkyl dimethyl ethyl ammonium bromide, Alkyl dimethyl ethylbenzyl ammonium chloride, Alkyl dimethyl isopropylbenzyl ammonium chloride, Alkyl trimethyl ammonium chloride, Alkyl 1 or 3 benzyl-1-(2-hydroxethyl)-2-imidazolinium chloride, Dialkyl methyl benzyl ammonium chloride, Dialkyl dimethyl ammonium chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy) ethyl dimethyl benzyl ammonium chloride, Dioctyl dimethyl ammonium chloride, Dodecyl bis(2-hydroxyethyl) octyl hydrogen ammonium chloride, Dodecyl dimethyl benzyl ammonium chloride, Dodecylcarbamoyl methyl dimethyl benzyl ammonium chloride, Heptadecyl hydroxyethylimidazolinium chloride, Hexahydro-1,3,5-tris(2-hydroxyethyl)-s-triazine, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysilyl quats, and Trimethyl dodecylbenzyl ammonium chloride.

8. Other Components

In some embodiments, a nanoemulsion adjuvant composition comprises one or more additional components that provide a desired property or functionality to the nanoemulsions. These components may be incorporated into the aqueous phase or the oil phase of the nanoemulsions and/or may be added prior to or following emulsification. For example, in some embodiments, the nanoemulsions further comprise phenols (e.g., triclosan, phenyl phenol), acidifying agents (e.g., citric acid (e.g., 1.5-6%), acetic acid, lemon juice), alkylating agents (e.g., sodium hydroxide (e.g., 0.3%)), buffers (e.g., citrate buffer, acetate buffer, and other buffers useful to maintain a specific pH), and halogens (e.g., polyvinylpyrrolidone, sodium hypochlorite, hydrogen peroxide).

Exemplary techniques for making a nanoemulsion are described below. Additionally, a number of specific, although exemplary, formulation recipes are also set forth herein.

In some embodiments, a nanoemulsion adjuvant is administered to a subject before, concurrent with or after administration of a composition comprising an immunogen (e.g., a pathogen and/or pathogen component (e.g., purified, isolated and/or recombinant pathogen peptide and/or protein)). The invention is not limited to the use of any one specific type of composition comprising an immunogen. Indeed, a variety of compositions comprising an immunogen (e.g., utilized for generating an immune response (e.g., for use as a vaccine)) may be utilized with a nanoemulsion adjuvant of the invention. In some embodiments, the composition comprising an immunogen comprises pathogens (e.g., killed pathogens), pathogen components or isolated, purified and/or recombinant parts thereof.

In some embodiments, a nanoemulsion adjuvant is administered to a subject before, concurrent with or after administration of a vaccine containing peptides (e.g., one generally well known in the art, as exemplified by U.S. Pat. Nos. 4,601,903; 4,599,231; 4,599,230; and 4,596,792; each of which is hereby incorporated by reference).

Formulation Techniques

Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, and U.S. Patent Application Nos. 20070036831, 20060251684, and 20050208083, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen. In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucliamellar lipid vesicles, micelles, and lamellar phases.

As described above, the present invention is not limited by the type of subject administered a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism. In some embodiments, the human subjects are subjects that are more likely to receive a direct exposure to pathogenic microorganisms or that are more likely to display signs and symptoms of disease after exposure to a pathogen (e.g., subjects with CF or asthma, subjects in the armed forces, government employees, frequent travelers, persons attending or working in a school or daycare, health care workers, an elderly person, an immunocompromised person, and emergency service employees (e.g., police, fire, EMT employees)). In some embodiments, any one or all members of the general public can be administered a composition of the present invention (e.g., to prevent the occurrence or spread of disease). For example, in some embodiments, compositions and methods of the present invention are utilized to treat a group of people (e.g., a population of a region, city, state and/or country) for their own health (e.g., to prevent or treat disease) and/or to prevent or reduce the risk of disease spread from animals (e.g., birds, cattle, sheep, pigs, etc.) to humans. In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition comprising a nanoemulsion of the present invention can be administered (e.g., to a subject (e.g., via pulmonary and/or mucosal route)) as a therapeutic or as a prophylactic to prevent microbial infection.

Therapeutics and Prophylactics

Furthermore, in preferred embodiments, a composition of the present invention induces (e.g., when administered to a subject) both systemic and mucosal immunity. Thus, in some preferred embodiments, administration of a composition comprising a nanoemulsion and *Streptococcus* (e.g., *Streptococcus pneumoniae*) antigen to a subject results in protection against an exposure (e.g., a mucosal exposure) to *Streptococcus*. Although an understanding of the mechanism is not necessary to practice the present invention and the present invention is not limited to any particular mechanism of action, mucosal administration (e.g., vaccination) provides protection against *Streptococcus* (e.g., *Streptococcus pneumoniae*) infection (e.g., that initiates at a mucosal surface). Although it has heretofore proven difficult to stimulate secretory IgA responses and protection against pathogens that invade at mucosal surfaces (See, e.g., Mestecky et al, Mucosal Immunology. 3ed edn. (Academic Press, San Diego, 2005)), in some embodiments, the present invention provides compositions and methods for stimulating mucosal immunity (e.g., a protective IgA response) from a pathogen (e.g., pathogenic species of *Streptococcus* (e.g., *Streptococcus pneumoniae*)) in a subject.

In some embodiments, the present invention provides a composition (e.g., a composition comprising a nanoemulsion and *Streptococcus* (e.g., *Streptococcus pneumoniae* antigen) to serve as a mucosal vaccine. In some embodiments, this material is produced with NE and killed whole cell bacteria of the genus *Streptococcus* (e.g., *Streptococcus pneumoniae* (e.g., killed using nanoemulsion, alcohol (e.g., ethanol), or other methods), isolated, purified and/or recombinant protein and/or saccharide component of *Streptococcus* (e.g., protein/peptide (e.g., *Streptococcus*-derived protein, live-virus-vector-derived protein, recombinant protein, recombinant denatured protein/antigens, small peptide segments protein/antigen). The ability to produce this formulation rapidly and administer it via mucosal (e.g., nasal) instillation provides a vaccine that can be used in large-scale administrations (e.g., to a population of a town, village, city, state or country). The present invention is not limited to any particular formulation (e.g., comprising a nanoemulsion and one or more recombinant *Streptococcus* proteins). For example, in some embodiments, the invention provides a nanoemulsion described herein combined with one or more recombinant *Streptococcus* proteins (e.g., PsaA, PiuA, PavA).

In some preferred embodiments, the present invention provides a composition for generating an immune response comprising a NE and an immunogen (e.g., a purified, isolated or synthetic *Streptococcus* protein or derivative, variant, or analogue thereof; or, one or more serotypes of *Streptococcus* (e.g., *Streptococcus pneumoniae* (e.g., killed and or inactivated whole cell bacteria). When administered to a subject, a composition of the present invention stimulates an immune response against the immunogen within the subject. Although an understanding of the mechanism is not necessary to practice the present invention and the present invention is not limited to any particular mechanism of action, in some embodiments, generation of an immune response (e.g., resulting from administration of a composition comprising a nanoemulsion and an immunogen) provides total or partial immunity to the subject (e.g., from signs, symptoms or conditions of a disease (e.g., strep throat, meningitis, bacterial *pneumoniae*, endocarditis, erysipelas and/or necrotizing fasciitis)). Without being bound to any specific theory, protection and/or immunity from disease (e.g., the ability of a subject's immune system to prevent or attenuate (e.g., suppress) a sign, symptom or condition of disease) after exposure to an immunogenic composition of the present invention is due to adaptive (e.g., acquired) immune responses (e.g., immune responses mediated by B and T cells following exposure to a NE comprising an immunogen of the present invention (e.g., immune responses that exhibit increased specificity and reactivity towards *Streptococcus* (e.g., *Streptococcus pneumoniae*)). Thus, in some embodiments, the compositions and methods of the present invention are used prophylactically or therapeutically to prevent or attenuate a sign, symptom or condition associated with *Streptococcus* (e.g., *Streptococcus pneumoniae*)).

In some embodiments, a NE comprising an immunogen (e.g., a *Streptococcus* (e.g., *Streptococcus pneumoniae*) antigen) is administered alone. In some embodiments, a composition comprising a NE and an immunogen (e.g., a *Streptococcus* (e.g., *Streptococcus pneumoniae*) antigen) comprises one or more other agents (e.g., a pharmaceutically acceptable carrier, adjuvant, excipient, and the like). In some embodiments, a composition for stimulating an immune response of the present invention is administered in a manner to induce a humoral immune response. In some embodiments, a composition for stimulating an immune response of the present invention is administered in a manner to induce a cellular (e.g., cytotoxic T lymphocyte) immune response, rather than a humoral response. In some embodiments, a composition comprising a NE and an immunogen of the present invention induces both a cellular and humoral immune response.

The present invention is not limited by the isotype or strain of *Streptococcus* (e.g., *Streptococcus pneumoniae*) used in a composition comprising a NE and immunogen. Indeed, each *Streptococcus* (e.g., *Streptococcus pneumoniae*) family member alone, or in combination with another family member, may be used to generate a composition comprising a NE and an immunogen (e.g., used to generate an immune response) of the present invention. Exemplary species of *Streptococcus* and isotypes of *Streptococcus pneumoniae* are described herein.

Thus, in some embodiments, the *Streptococcus* (e.g., *Streptococcus pneumoniae*) strain utilized is a modified (e.g., genetically modified (e.g., naturally modified via natural selection or modified using recombinant genetic techniques)) strain that displays greater pathogenic capacity (e.g., causes more sever *Streptococcus*—(e.g., *Streptococcus pneumoniae*)—induced disease (e.g., comprising enhanced and/or more severe strep throat, meningitis, etc.)). In some embodiments, any one or more members of the *Streptococcus* genus is utilized in an immunoreactive composition of the invention including but not limited to *S. pneumoniae, S. mutans, S. mitis, S. sanguinis, S. salivarius, S. viridans, S. salivarius* ssp. *thermophilus, S. constellatus, S. pyogenes, S. agalactiae, S. zooepidemicus, Streptococcus bovis* and *Streptococcus equines, Streptococcus canis*, as well as former Group D Streptococci including *S. faecalis, S. faecium, S. durans*, and *S. avium*.

The present invention is not limited by the *Streptococcus* (e.g., *Streptococcus pneumoniae*) isotype and/or strain used. Indeed, a variety of *Streptococcus* (e.g., *Streptococcus pneumoniae*) strains are contemplated to be useful in the present invention including, but not limited to, classical strains, attenuated strains, non-replicating strains, modified strains (e.g., genetically or mechanically modified strains (e.g., to become more or less virulent)), or other serially diluted strains of *Streptococcus* (e.g., *Streptococcus pneumoniae*). A composition comprising a NE and immunogen may comprise one or more strains of *Streptococcus* (e.g., *Streptococcus pneumoniae*) and/or other type of *Streptococcus* (e.g., *Streptococcus pneumoniae*). Additionally, a composition comprising a NE and immunogen may comprise one or more strains of *Streptococcus* (e.g., *Streptococcus pneumoniae*), and, in addition, one or more strains of a non-Streptococcus (e.g., *Streptococcus pneumoniae*) immunogen.

In some embodiments, the immunogen may comprise one or more antigens derived from a pathogen (e.g., *Streptococcus* (e.g., *Streptococcus pneumoniae*)). For example, in some embodiments, the immunogen is a purified, recombinant, synthetic, or otherwise isolated protein (e.g., added to the NE to generate an immunogenic composition). Similarly, the immunogenic protein may be a derivative, analogue or otherwise modified (e.g., PEGylated) form of a protein from a pathogen.

The present invention is not limited by the particular formulation of a composition comprising a NE and immunogen of the present invention. Indeed, a composition comprising a NE and immunogen of the present invention may comprise one or more different agents in addition to the NE and immunogen. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a NE and immunogen of the present invention comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition) comprising a NE and immunogen). For example, in some embodiments, suitable adjuvants include an aluminum salt such as aluminum hydroxide gel (alum) or aluminum phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In some embodiments, it is preferred that a composition comprising a NE and immunogen of the present invention comprises one or more adjuvants that induce a Th1-type response. However, in other embodiments, it will be preferred that a composition comprising a NE and immunogen of the present invention comprises one or more adjuvants that induce a Th2-type response.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th1-type immune response in a subject comprising administering to a subject a composition comprising a NE and an immunogen. However, in other embodiments, the present invention provides a method of stimulating a Th2-type immune response in a subject (e.g., if balancing of a T cell mediated response is desired) comprising administering to a subject a composition comprising a NE and an immunogen. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4): 392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja Saponaria* Molina), and fractions thereof (See, e.g., U.S. Pat. No. 5,057, 540; Kensil, Crit. Rev Ther Drug Carrier Syst, 1996, 12 (1-2):1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1999, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a NE solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an E. Coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising a NE and immunogen of the present invention.

Additional examples of adjuvants that find use in the present invention include poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

Adjuvants may be added to a composition comprising a NE and an immunogen, or, the adjuvant may be formulated with carriers, for example liposomes, or metallic salts (e.g., aluminium salts (e.g., aluminium hydroxide)) prior to combining with or co-administration with a composition comprising a NE and an immunogen.

In some embodiments, a composition comprising a NE and an immunogen comprises a single adjuvant. In other embodiments, a composition comprising a NE and an immunogen comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a NE and an immunogen of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a NE and immunogen) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a NE and an immunogen of the present invention can be used therapeutically (e.g., to enhance an immune response) or as a prophylactic (e.g., for immunization (e.g., to prevent signs or symptoms of disease)). A composition comprising a NE and an immunogen of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some preferred embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science arid Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., mucosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a NE and an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition comprising a NE and immunogen is provided. Enteric formulations such as gastro resistant capsules for oral administration, suppositories for rectal or vaginal administration also form part of this invention. Compositions of the present invention may also be administered via the oral route. Under these circumstances, a composition comprising a NE and an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising a NE and an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a composition comprising a NE and an immunogen may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using a composition comprising a NE and immunogen of the present invention).

For example, in some embodiments, a composition comprising a NE and an immunogen is administered to a mucosal surface of a subject in either a priming or boosting vaccination regime. Alternatively, in some embodiments, a composition comprising a NE and an immunogen is administered systemically in either a priming or boosting vaccination regime. In some embodiments, a composition comprising a NE and an immunogen is administered to a subject in a priming vaccination regimen via mucosal administration and a boosting regimen via systemic administration. In some embodiments, a composition comprising a NE and an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising a NE and an immunogen may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a NE and an immunogen of the present invention may be used to protect and/or treat a subject susceptible to, or suffering from, a disease by means of administering a compositions comprising a NE and an immunogen by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. No. 4,596,556; U.S. Pat. No. 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., Streptococcal bacteria (e.g., *Streptococcus pneumoniae*)). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals). In some embodiments, the present invention provides a method to elicit an immune response (e.g., protective immune response) in infants (e.g., from about 0-2 years old) by administering to the infant a safe and effective amount of an immunogenic composition of the invention (e.g., a pediatric vaccine). Further embodiments of the invention include the provision of the immunogenic S. pneumoniae compositions of the invention for use in medicine and the use of the S. pneumoniae compositions of the invention in the manufacture of a medicament for the prevention (or treatment) of pneumococcal disease.

In yet another embodiment, the present invention is provides a method to elicit an immune response (e.g., a protective immune response) in the elderly population (e.g., in a subject 50 years or over in age, typically over 55 years and more generally over 60 years) by administering a safe and effective amount of an immunogenic composition of the invention.

A composition of the present invention may be formulated for administration by any route, such as mucosal, oral, topical, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl)pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipuritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the NE and immunogen of the formulation. In some embodiments, immunostimulatory compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a NE and an immunogen is co-administered with one or more antibiotics. For example, one or more antibiotics may be administered with, before and/or after administration of a composition comprising a NE and an immunogen. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erythromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a composition comprising a NE and an immunogen with one or more additional active and/or immunostimulatory agents (e.g., a composition comprising a NE and a different immunogen, an antibiotic, anti-oxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising a NE and immunogen is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an immunogen or organism from which the immunogen is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of a composition comprising a NE and immunogen of the present invention) may have a stronger immune response to an immunogen than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In preferred embodiments, a composition comprising a NE and an immunogen of the present invention comprises a suitable amount of the immunogen to induce an immune response in a subject when administered to the subject. In preferred embodiments, the immune response is sufficient to provide the subject protection (e.g., immune protection) against a subsequent exposure to the immunogen or the microorganism (e.g., Streptococcal bacteria (e.g., *Streptococcus pneumoniae*)) from which the immunogen was derived. The present invention is not limited by the amount of immunogen used. In some preferred embodiments, the amount of immunogen (e.g., Streptococcal bacteria (e.g., *Streptococcus pneumoniae*) or one or more component parts thereof) in a composition comprising a NE and immunogen (e.g., for use as an immunization dose) is selected as that amount which induces an immunoprotective response without significant, adverse side effects. The amount will vary depending upon which specific immunogen or combination thereof is/are employed, and can vary from subject to subject, depending on a number of factors including, but not limited to, the species, age and general condition (e.g., health) of the subject, and the mode of administration.

In some embodiments, each dose (e.g., of a composition comprising a NE and an immunogen (e.g., administered to a subject to induce an immune response (e.g., a protective immune response (e.g., protective immunity))) comprises between about $10^5$ and $10^8$ colony forming units (CFU) of *Streptococcus* (e.g., *Streptococcus pneumoniae*) of killed/inactivated bacteria, although greater (e.g., about $10^9$, $10^{10}$, $10^{11}$, $10^{12}$ or more) and lesser (e.g., about $10^4$, $10^3$, $10^2$ or fewer) CFU of *Streptococcus* (e.g., *Streptococcus pneumoniae* (e.g., killed whole *Streptococcus pneumoniae*) may also be utilized. In some embodiments, a nanoemulsion solution is utilized to inactivate the *Streptococcus* (e.g., *Streptococcus pneumoniae*). In some embodiments, a nanoemulsion solution is utilized to inactivate the *Streptococcus* (e.g., *Streptococcus pneumoniae*). In some embodiments, the nanoemulsion comprises $W_{80}5EC$. In some embodiments, the immunity protects the subject from displaying signs or symptoms of disease caused by *Streptococcus* (e.g., *Streptococcus pneumoniae*). In some embodiments, the immunity protects the subject from challenge with a subsequent exposure to live *Streptococcus* (e.g., *Streptococcus pneumoniae*). In some embodiments, each dose (e.g., administered to a subject to induce and immune response)) comprises between 10 and $10^{10}$ CFU of *Streptococcus* (e.g., *Streptococcus pneumoniae*) per dose. In some embodiments, each dose comprises between $10^5$ and $10^8$ CFU of *Streptococcus* (e.g., *Streptococcus pneumoniae*) per dose. In some embodiments, each dose comprises between $10^3$ and $10^5$ CFU of *Streptococcus* (e.g., *Streptococcus pneumoniae*) per dose. In some embodiments, each dose comprises between $10^5$ and $10^8$ CFU of *Streptococcus* (e.g., *Streptococcus pneumoniae*) per dose; in some embodiments, each dose comprises $10^5$ CFU of *Streptococcus* (e.g., *Streptococcus pneumoniae*) per dose. In some embodiments, each dose comprises $10^6$ CFU of *Streptococcus* (e.g., *Streptococcus pneumoniae*) per dose. In some embodiments, each dose comprises $10^7$ CFU of *Streptococcus* (e.g., *Streptococcus pneumoniae*) per dose. In some embodiments, each dose comprises more than $10^8$ CFU of *Streptococcus* (e.g., *Streptococcus pneumoniae*) per dose. In some preferred embodiments, each dose comprises $10^8$ CFU of *Streptococcus* (e.g., *Streptococcus pneumoniae*) per dose.

In some embodiments, each dose (e.g., of a composition comprising a NE and an immunogen (e.g., administered to a subject to induce an immune response (e.g., a protective immune response (e.g., protective immunity))) comprises 0.05-5000 µg of an additional immunogen (e.g., recombinant and/or purified protein, adjuvant (e.g., cholera toxin), etc.). In some embodiments, each dose will comprise 1-500 µg, in some embodiments, each dose will comprise 350-750 µg, in some embodiments, each dose will comprise 50-200m, in some embodiments, each dose will comprise 25-75 µg of immunogen (e.g., recombinant and/or purified protein). In some embodiments, each dose comprises an amount of the immunogen sufficient to generate an immune response. An effective amount of the immunogen in a dose need not be quantified, as long as the amount of immunogen generates an immune response in a subject when administered to the subject.

In some embodiments, it is expected that each dose (e.g., of a composition comprising a NE and an immunogen (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria, or recombinant and/or purified protein). In some embodiments, an initial or prime administration dose contains more immunogen than a subsequent boost dose In some embodiments, when a NE of the present invention is utilized to inactivate a live microorganism, each dose (e.g., administered to a subject to induce and immune response)) comprises between 10 and $10^9$ CFU of the microorganism per dose; in some embodiments, each dose comprises between $10^5$ and $10^8$ CFU of the microorganism per dose; in some embodiments, each dose comprises between $10^3$ and $10^5$ CFU of the microorganism per dose; in some embodiments, each dose comprises between $10^2$ and $10^4$ CFU of the microorganism per dose; in some embodiments, each dose comprises 10 CFU of the microorganism per dose; in some embodiments, each dose comprises $10^2$ CFU of the microorganism per dose; and in some embodiments, each dose comprises $10^4$ CFU of the microorganism per dose. In some embodiments, each dose comprises more than $10^9$ CFU of the microorganism per dose. In some preferred embodiments, each dose comprises $10^3$ CFU of the microorganism per dose.

The present invention is not limited by the amount of NE used to inactivate live microorganisms (e.g., Streptococcal bacteria (e.g., *S. pneumoniae*)). In some embodiments, a 0.1%-5% NE solution is used, in some embodiments, a 5%-20% NE solution is used, in some embodiments, a 20% NE solution is used, and in some embodiments, a NE solution greater than 20% is used order to inactivate a pathogenic microorganism. In preferred embodiments, a 15% NE solution is used.

Similarly, the present invention is not limited by the duration of time a live microorganism is incubated in a NE of the present invention in order to become inactivated. In some embodiments, the microorganism is incubated for 1-3 hours in NE. In some embodiments, the microorganism is incubated for 3-6 hours in NE. In some embodiments, the microorganism is incubated for more than 6 hours in NE. In preferred embodiments, the microorganism is incubated for 3 hours in NE (e.g., a 10% NE solution). In some embodiments, the incubation is carried out at 37° C. In some embodiments, the incubation is carried out at a temperature greater than or less than 37° C. The present invention is also not limited by the amount of microorganism used for inactivation. The amount of microorganism may depend upon a number of factors including, but not limited to, the total amount of immunogenic composition (e.g., NE and immunogen) desired, the concentration of solution desired (e.g., prior to dilution for administration), the microorganism and the NE. In some preferred embodiments, the amount of microorganism used in an inactivation procedure is that amount that produces the desired amount of immunogen (e.g., as described herein) to be administered in a single dose (e.g., diluted from a concentrated stock) to a subject.

In some embodiments, a composition comprising a NE and an immunogen of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the NE and immunogen present in the concentrated composition. In some preferred embodiments, a subject is administered in a single dose a composition comprising 1% of the NE and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a NE and an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Generally, the emulsion compositions of the invention will comprise at least 0.001% to 100%, preferably 0.01 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 98% of emulsion per ml of liquid composition. It should be understood that a range between any two figures listed above is specifically contemplated to be encompassed within the metes and bounds of the present invention. Some variation in dosage will necessarily occur depending on the condition of the specific pathogen and the subject being immunized.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of mucosal and other routes of delivery. As is readily apparent, the compositions of the present invention are useful for preventing and/or treating a wide variety of diseases and infections caused by viruses, bacteria, parasites, and fungi, as well as for eliciting an immune response against a variety of antigens. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest. If polyclonal antibodies are desired, a selected mammal, (e.g., mouse, rabbit, goat, horse, etc.) can be immunized with the compositions of the present invention. The animal is usually boosted 2-6 weeks later with one or more—administrations of the antigen. Polyclonal antisera can then be obtained from the immunized animal and used according to known procedures (See, e.g., Jurgens et al., J. Chrom. 1985, 348:363-370).

In some embodiments, the present invention provides a kit comprising a composition comprising a NE and an immunogen. In some embodiments, the kit further provides a device for administering the composition. The present invention is not limited by the type of device included in the kit. In some embodiments, the device is configured for nasal application of the composition of the present invention (e.g., a nasal applicator (e.g., a syringe) or nasal inhaler or nasal mister). In some embodiments, a kit comprises a composition comprising a NE and an immunogen in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit component are located in a single container (e.g., vial or tube) with other components of the same kit being located in a separate container (e.g., vial or tube). In some embodiments, a kit comprises a buffer. In some embodiments, the kit further comprises instructions for use.

EXAMPLES

The following examples serve to illustrate certain preferred embodiments and aspects of the present invention and are not to be construed as limiting the scope thereof.

In the experimental disclosure which follows, the following abbreviations apply: eq (equivalents); µ (micron); M (Molar); µM (micromolar); mM (millimolar); N (Normal); mol (moles); mmol (millimoles); µmol (micromoles); nmol (nanomoles); g (grams); mg (milligrams); µg (micrograms); ng (nanograms); L (liters); ml (milliliters); µl (microliters); cm (centimeters); mm (millimeters); µm (micrometers); nM (nanomolar); ° C. (degrees Centigrade); and PBS (phosphate buffered saline).

Example 1

Immunogenic *Streptococcus pneumoniae* Compositions

Experimental Design and Materials and Methods.

Outbred CD-1 or C57/B6 (8 groups; 6 mice per group) were intranasally immunized with 7.5 µL or 0.1 µL WCPAg in 1, 5, 10 and 20% NE. WCPAg was generated as follows: strain RX1, a capsule-negative mutant derived from a *pneumococcus* capsular serotype 2 (e.g., an autolysin (lytA)-negative mutant of Rx1 (Rx1AL$^-$)) grown at 37° C. in Todd-Hewitt broth supplemented with 0.5% yeast extract (THY) and 0.3 µg of erythromycin/ml to about $10^9$ cells/ml, washed and suspended in saline at 10% of the original volume, and then mixed 3:7 (volume/volume) with ethanol, washed and resuspended in saline, and then frozen for later use.

The mice were given a volume of 12 µL (6 µL per nare) delivered manually into the nasal cavity of the mouse. Control groups were: 7.5 µL, WCPAg in PBS, cholera toxin (CT), or Alum (delivered intramuscularly); 0.1 µL WCPAg in PBS; 20% NE alone.

The study design is presented in table 1.

TABLE 1

Design for *S. pneumoniae* Efficacy

| Treatment Day 0, Week 4, Week 8 | Conc. WCPAg (cells/ml) | Cells/ inoculum | Volume (μl) | N (CD1) |
|---|---|---|---|---|
| 7.5 μl WCPAg + 1% NE | $1.3 \times 10^{10}$ | $10^8$ | 12 | 6 |
| 7.5 μl WCPAg + 5% NE | $1.3 \times 10^{10}$ | $10^8$ | 12 | 6 |
| 7.5 μl WCPAg + 10% NE | $1.3 \times 10^{10}$ | $10^8$ | 12 | 6 |
| 7.5 μl WCPAg + 20% NE | $1.3 \times 10^{10}$ | $10^8$ | 12 | 6 |
| 0.1 μl WCPAg + 1% NE | $1 \times 10^{10}$ | $10^6$ | 12 | 6 |
| 0.1 μl WCPAg + 5% NE | $1 \times 10^{10}$ | $10^6$ | 12 | 6 |
| 0.1 μl WCPAg + 10% NE | $1 \times 10^{10}$ | $10^6$ | 12 | 6 |
| 0.1 μl WCPAg + 20% NE | $1 \times 10^{10}$ | $10^6$ | 12 | 6 |
| 7.5 μl WCPAg + 1xPBS | $1.3 \times 10^7$ | $10^8$ | 12 | 8 |
| 20% NE | | | 12 | 4 |
| 7.5 μl WCPAg + Alum IM | $1.3 \times 10^7$ | $10^8$ | 12 | 2 |
| 7.5 ml WCPAg + CT | $1.3 \times 10^7$ | $10^8$ | 12 | 4 |
| 0.1 μl WCPAg + 1xPBS | $1 \times 10^{10}$ | $10^6$ | 12 | 8 |

Mice were vaccinated at week 0, 4 and 8 (See, e.g., Malley, et al. (2005) Proc Natl Acad Sci USA. March 29; 102(13): 4848-53). Blood samples were obtained via saphenous vein bleed at weeks 0, 2, 4, 6, 8, and 10. IgG antibodies against the lysed whole bacterium were assayed via ELISA after each bleed week.

At week 12, mice were given rifampin subcutaneously to clear any nasal colonization. Seven days post rifampin, mice were challenged with $1 \times 10^5$ CFU live *S. pneumoniae*/mouse and monitored daily for weight and temperature. On day 7 after challenge, the mice were sacrificed and cardiac bleed was taken for CBC and IgG titers, heads were preserved for histology and retrograde nasophyringeal wash was taken for *S. pneumoniae* colony counts on blood-agar plates. IgG end-titer ELISA was performed in-house using standard assays known in the art. CBC was performed at the University of Michigan Unit for Laboratory Animal Medicine (ULAM) per standard procedures known in the art Test Formulation. Vaccine formulations were prepared by vigorously mixing WCPAg and NE or Alum or CT in 10×PBS and sterile water for injection for about 20 seconds just prior to immunization (30 to 60 minutes) (See FIG. 1 for formulations).

Immunization Procedures. Mice were vaccinated intranasally (I.N.) or intramuscularly (I.M.) with 3 administrations of vaccine and antibody responses were measured at two week intervals over a period of 12 weeks. For I.N. immunization, animals were anaesthetized with Isoflurane (IMPAC6) and held in an inverted position until 6 μL of vaccine, delivered with a pipette tip, were completely inhaled. For I.M. vaccination, mice were anaesthetized with Isoflurane (IMPAC6) and 124 of WCPAg/Alum vaccine was injected into the epaxial muscle.

Blood Sample Collection. Blood samples were obtained from the saphenous vein at various time points during the course of the trials. The final sample was obtained by cardiac puncture from euthanized, premorbid mice. Serum was separated from the blood by centrifugation at 1500×g for 5 minutes after coagulation. Serum was stored at −20° C. until used for ELISA. For CBC, blood was collected after cardiac puncture and placed into heparinized tubes with continuous rocking until delivery to ULAM.

Weight/Temperature Monitoring. Weight and body core temperature (rectal thermometer BAT-12) temperatures were taken 5-7 days after challenge.

Rifampin Administration. Two weeks following the last immunization, animals in all groups received 1 mg of rifampin subcutaneously on two consecutive days to eliminate pneumococcal colonization.

Retrograde Nasopharyngeal Wash. Nasopharyngeal wash was obtained from mice euthanized by Isoflurane inhalation. After the trachea was dissected, a 22-gauge catheter (Angiocath, B-D) attached to a 1 ml syringe was inserted into the trachea further to the nasal cavity. The nares of the mice were washed with 1 μL PBS and solution was let to fall onto a blood agar plate coated with gentamycin.

Analysis of IgG titers: ELISA for anti-*S. pneumoniae* antibodies was utilized to determine IgG titers. Preparation of WCPAg-coated ELISA Plates. Coating buffer, 0.05M carbonate-bicarbonate buffer (pH 9.6), was made from carbonate-bicarbonate buffer capsules (SIGMA) by dissolving the in double distilled water according to manufacturer's instructions. *S. pneumoniae* lysate (whole bacterium lysed in non-ionic lysis buffer) was diluted in coating buffer and 100 μL per well was added to 96-well plates (Nunc, Maxisorb Plates). Plates were incubated overnight and kept at 4° C. until used. Stored plates were warmed up ½ hour at 37° C. and antigen solution was removed by inversion and tamping on paper towels. The plates were blocked with 1% milk in PBS (1004 per well) and incubated at 1 hour at 37° C. Blocking solution was removed from wells just before diluted serum was added.

Preparation of the primary antibody dilutions. Mouse sera was diluted in 0.1% BSA in PBS. 1004 of the diluted serum was added per well in duplicate and incubated overnight at 4° C. The next day, the plates were warmed for ½ hour at 37° C. The serum dilutions were removed by inversion/tamping and washed 3× with ELISA wash buffer (Quantikine, R&D Systems).

Preparation of a recommended dilution of secondary antibody conjugate. Secondary antibody (goat anti-mouse F(c) alkaline-phosphatase conjugated (Rockland) was diluted at 1:1000 in 0.1% BSA in PBS. 100 μL of the diluted secondary antibody was added to each well and incubated 1 hour at 37° C. The secondary antibody was removed by inversion/tamping and the plate washed 3 times with ELISA wash buffer (Quantikine, R&D Systems).

Preparation of alkaline phosphatase substrate solution. Sigmafast P-Nitrophenyl Phosphate Tablets (pNPP, SIGMA) were dissolved in double distilled water according to the manufacturer's recommendations. After removing the last wash, 100 μL of pNPP solution was added to each well incubated and read every ½ hour until saturation was achieved. The timepoint closest to saturation was chosen as analysis time.

End-point determination. The antibody endpoint titers are defined as the reciprocal of the highest serum dilution which gives a reading above cutoff value determined by the dilution of control sera and plate background (passes at least two standard deviations above average for background wells, See, e.g., Frey, et al. (1998) Journal of Immunological Methods 221:35-41; Classen, et al. (1987) Journal of Clinical Microbiology. 25:600).

Example 2

Distribution of Anti-*S. pneumoniae* Antibody Titers at 8 Weeks after Two Vaccinations FIG. 2 shows anti-*S. pneumoniae* IgG titer distributions at week 8, after two intranasal vaccine doses given one month apart on weeks 0 and 4, for experimental and control groups. All mice vaccinated with $10^8$ CFU WCPAg plus varying concentrations of nanoemulsion obtained a serum antibody titer of $5 \times 10^3$ or greater, with a maximum of $10^5$ and an average across all groups of 7×10⁵. Titers for individual animals (circles) and mean serum titer per group (dash) are shown (See FIG. 2).

Example 3

Figure 3:
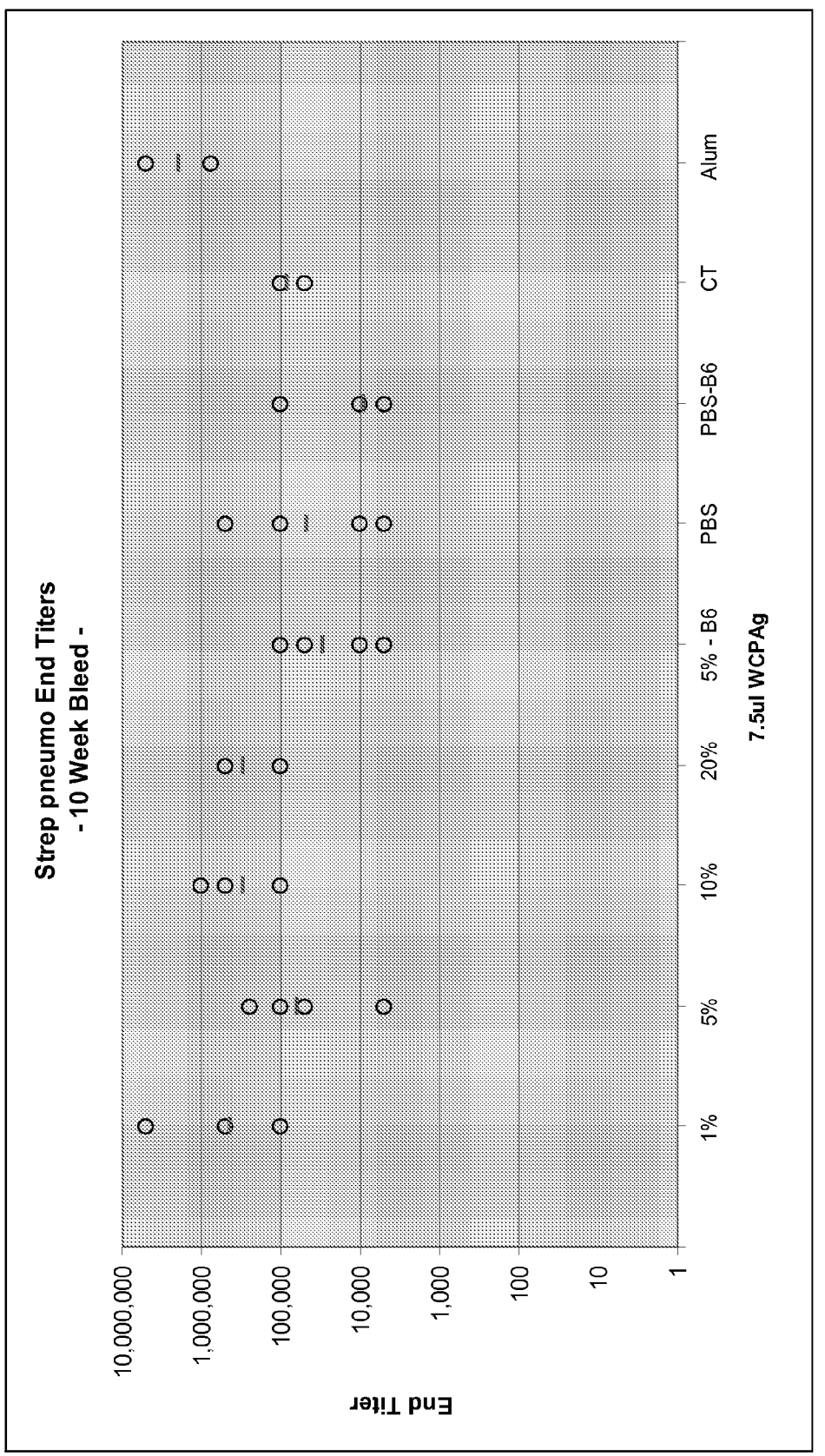
FIG. 3 shows the distribution of anti-*S. pneumoniae* antibody titers at 10 weeks after three vaccinations of A) 7.5 µl or B) 0.1 µl of *S. pneumoniae* antigen.

Distribution of Anti-*S. pneumoniae* Antibody Titers at 10 Weeks after Three Vaccinations FIG. 3 shows Anti-*S. pneumoniae* IgG titer distributions at week 10, after three intranasal vaccine doses given one month apart on weeks 0, 4, and 8 for experimental and control groups. All mice vaccinated with $10^8$ CFU WCPAg plus varying concentrations of nanoemulsion obtained a serum antibody titer of $5 \times 10^3$ or greater, with a maximum of $5 \times 10^6$ and an average across all $10^8$ CFU/vaccine groups of $4 \times 10^5$. Titers for individual animals (circles) and mean serum titer per group (dash) are shown (See FIG. 3).

Example 4

Nanoemulsion Utilized to Adjuvant Ethanol Killed Whole Cell *S. pneumoniae*

Figure 5:
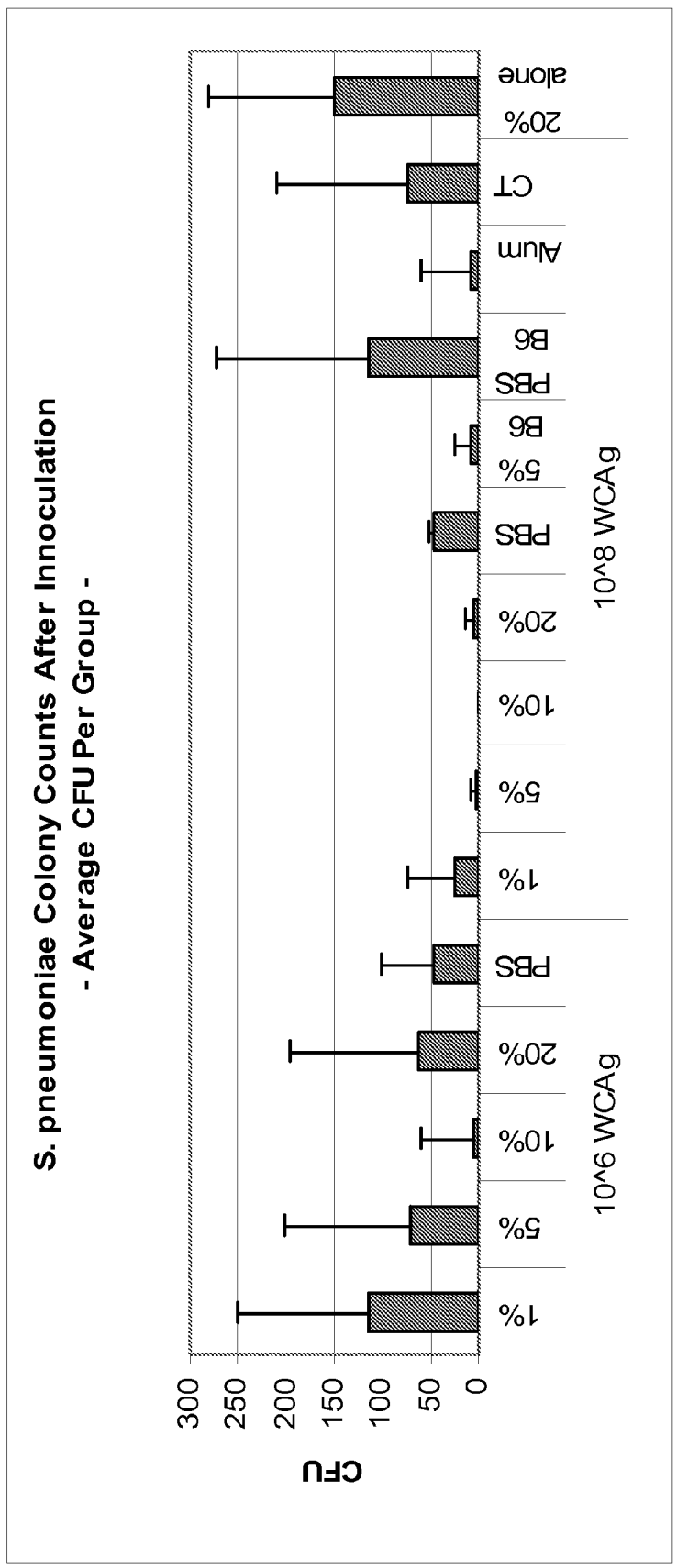
FIG. 5 shows results of a post-mortem nasalpharyngeal lavage that was performed at 12 weeks (1 week following challenge). The lavagent was plated on selective media and wildtype 6B *S. pneumoniae* were enumerated. WCAg=whole cell antigen. Data

Unless otherwise described herein, materials and methods indicated in Example 1 were utilized. Ethanol inactivated whole cell *S. pneumoniae* antigen (either $10^6$ or $10^8$ cells) was mixed with $W_{80}5EC$ nanoemulsion (ranging from 1% to 20%). This mixture was used to intranasally vaccinate (6 µl/nare) 8 week old outbred CD-1 mice (Jackson Labs, Bar arbor, ME). The mice were vaccinated and then boosted at 4 weeks following prime vaccination. The mice were nasally inoculated with $10^8$ live wildtype strain 6B *S. pneumoniae* at 11 weeks and sacrificed for colony enumeration at 12 weeks. Serum anti-pneumococcal IgG titers, as measured by ELISA, were found to be 1 to 1.5 logs greater than negative controls and approached within 0.5 log of positive (alum) control (See FIG. 4). The high serum titers in the high antigen dose group correlated with increased ability to eradicate intranasal colonization following challenge with wild-type *S. pneumoniae* (See FIG. 5).

Example 5

Compositions and Methods Utilizing Nanoemulsion Inactivated/Killed Whole Cell *S. pneumoniae*

Nanoemulsion was utilized to kill and/or inactivate live *S. pneumoniae*, which was then subsequently administered to subjects to generate immune response to nanoemulsion killed *S. pneumoniae* compositions. In order to evaluate the microbiocidal activity of nanoemulsion against *S. pneumoniae*, $1 \times 10^8$ live, acapsular LytA-*S. pneumoniae* mutant was mixed with varying concentrations of nanoemulsion ($W_{80}5EC$, 1%, 5%, 10% or 20%). The bacteria were incubated with NE for 30 minutes, 1 hour or 3 hours. The nanoemulsion was separated by centrifugation and the killed/inactivated whole cell acapsular LytA-*S. pneumoniae* pellets were washed to remove any remaining NE. Resuspended pellets were plated on blood agar for colony enumeration. Complete inactivation of the *S. pneumoniae* was noted at all time points (See FIG. 6).

A composition comprising nanoemulsion killed *S. pneumoniae* was utilized to generate immune response in subjects. Two different concentrations of nanoemulsion (5% and 15%) were utilized to to inactivate $10^7$ or $10^9$ live, acapsular LytA-*S. pneumoniae* mutant cells. For comparison, bacteria were also inactivated with ethanol (EI). Inactivation was verified using plate culture.

Figure 8:
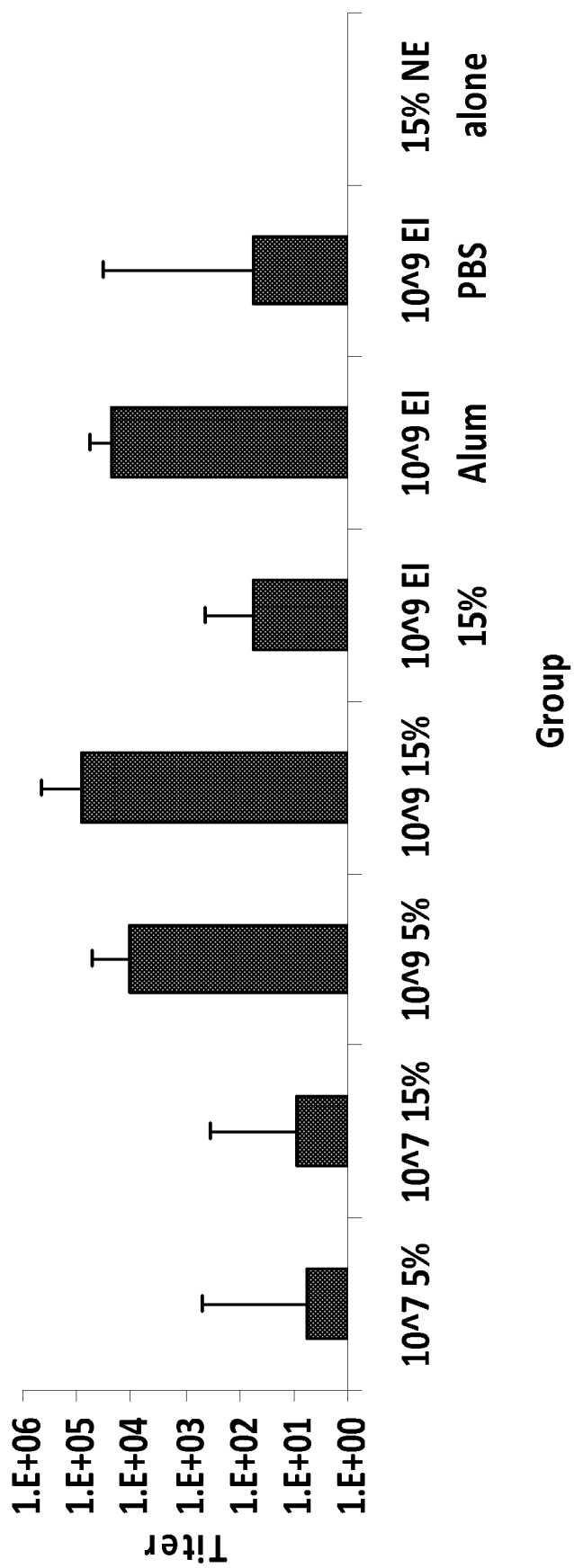
FIG. 8 shows serum anti-*S. pneumoniae* IgG antibodies in CD-1 mice measured at 8 weeks after primary immunization. Data presented as endpoint titters (+/−sd).
Figure 9:
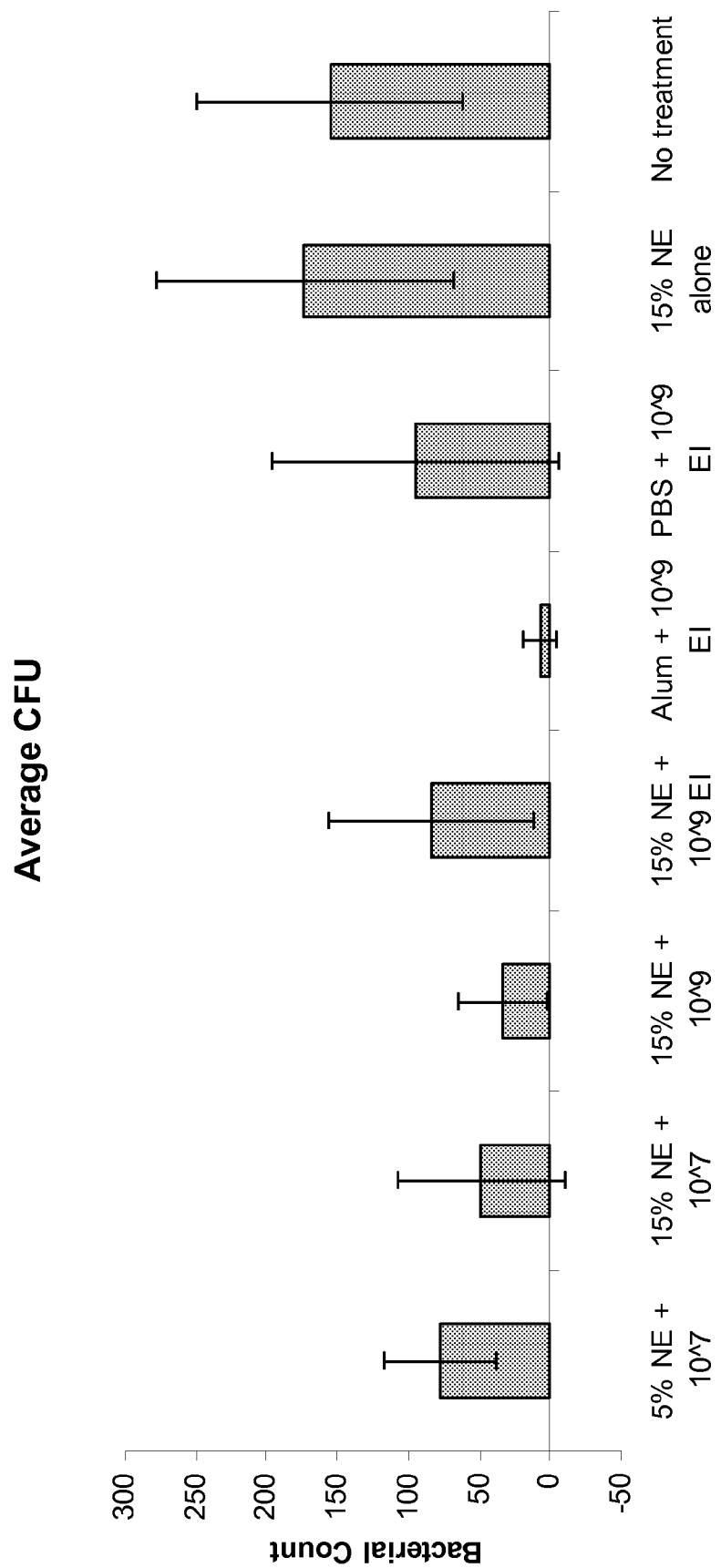
FIG. 9 shows results of a post-mortem nasalpharyngeal lavage performed at 9 weeks (1 week following challenge. The lavagent was plated on selective media and wildtype 6B *S. pneumoniae* were enumerated. Data presented as endpoint titters (+/−sd).

Following the inactivation procedure, mice were immunized with the combined inactivated *S. pneumoniae* and NE. Immunizations were delivered intranasally except for positive (Alum) control. The mice were primed and then boosted at 4 weeks (See FIG. 7). The mice were nasally inoculated with $10^8$ live wildtype strain 6B *S. pneumoniae* at 8 weeks and sacrificed for colony enumeration at 9 weeks. Serum anti-pneumococcal IgG titers were observed that approached $10^5$ in mice vaccinated with 15% NE-$10^9$ inactivated bacteria. These titers were equivalent or greater than (alum) control mice (See FIG. 8). The high serum titers in the high antigen dose group correlated with increased ability to eradicate intranasal colonization following challenge with wild-type *S. pneumoniae* (See FIG. 9).

Thus, in some embodiments, the present invention provide that nasal administration of a whole cell *Streptococcus pneumoniae* antigen (WCPAg, killed and/or inactivated by mixing with ethanol and/or nanoemulsion) mixed with nanoemulsion induces IgG response and eradicates upper respiratory colonization.

Example 6

Identification of *S. pneumoniae* Immunogens

Although an understanding of a mechanism is not necessary to practice the present invention, and the invention is not limited to any particular mechanism of action, experiments were conducted during development of embodiments of the invention in order to further characterize and/or identify immunoreactive proteins present in inactivated *S. pneumoniae*, (e.g., inactivated using nanoemulsion or ethanol).

Figure 10:
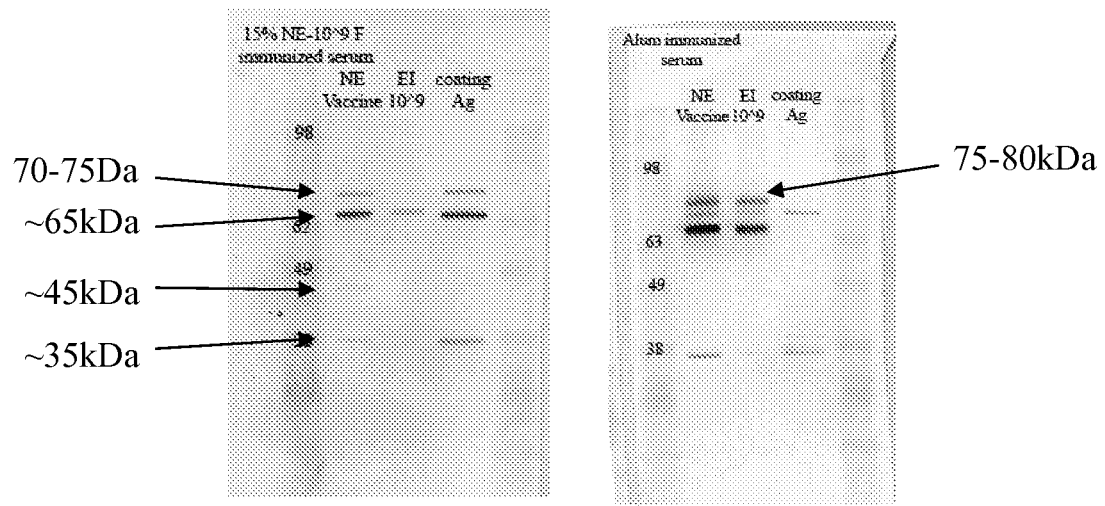
FIG. 10 shows western blots of pneumococcal antigens probed with either serum from mice vaccinated with NE-*S. pneumo* (left) or Alum-*S. pneumo* (right). Lane 1 and 5 represent the molecular weight ladder. Lane 2 represents *S. pneumoniae* inactivated with NE. Lane 3 represents ethanol inactivated *S. pneumoniae*. Lane 4 represents wildtype 6B antigen.

Experiments were designed to identify potential protective antigens. Work involved identification of immunoreactive proteins via western blotting. NE inactivated *S. pneumoniae*, ethanol inactivated *S. pneumoniae*, and wildtype 6B inactivated protein were electrophoretically separated and probed with either serum from mice vaccinated with 15% NE-$10^9$ *S. pneumoniae* or 0.5 mg/kg Alum-*S. pneumoniae* (See FIG. 10). Bands at several molecular weights corresponding to known conserved or semi-conserved pneumococcal proteins were identified (e.g., PsaA, PiuA, PavA).

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:
1. A method of inducing an immune response to *Streptococcus pneumoniae* in a subject comprising:
   a) providing an immunogenic composition comprising a nanoemulsion and an immunogen, wherein said nanoemulsion comprises a non-ionic surfactant, ethanol, cetylpyridinium chloride (CPC), oil and water, and wherein said immunogen comprises killed whole cell *Streptococcus pneumoniae*; and b) intranasally administering said composition to said subject under conditions such that said subject generates an immune response to *Streptococcus pneumonia*, wherein said immune response comprises generation of serum anti-*Streptococcus pneumoniae* IgG antibody titers of at least $10^4$ in the subject eight weeks post intranasal administration.

2. The method of claim 1, wherein the intranasal administration comprises contacting nasal mucosa.

3. The method of claim 1, wherein said composition is administered to said subject under conditions such that between $10^6$ and $10^8$ CFU of killed *Streptococcus pneumoniae* is present in a dose administered to said subject.

4. The method of claim 1, wherein said immune response protects said subject from displaying signs or symptoms of disease caused by *Streptococcus pneumoniae*.

5. The method of claim 1, wherein said immune response protects said subject from challenge with a subsequent exposure to live *Streptococcus pneumoniae*.

* * * * *